United States Patent
Rezazadegan Tavakoli et al.

(10) Patent No.: US 12,036,036 B2
(45) Date of Patent: Jul. 16, 2024

(54) HIGH-LEVEL SYNTAX FOR SIGNALING NEURAL NETWORKS WITHIN A MEDIA BITSTREAM

(71) Applicant: Nokia Technologies Oy, Espoo (FI)

(72) Inventors: Hamed Rezazadegan Tavakoli, Espoo (FI); Francesco Cricrì, Tampere (FI); Emre Baris Aksu, Tampere (FI); Miska Matias Hannuksela, Tampere (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 17/649,915

(22) Filed: Feb. 3, 2022

(65) Prior Publication Data
US 2022/0256227 A1 Aug. 11, 2022

Related U.S. Application Data

(60) Provisional application No. 63/146,224, filed on Feb. 5, 2021.

(51) Int. Cl.
*H04N 21/435* (2011.01)
*A61B 5/00* (2006.01)
(Continued)

(52) U.S. Cl.
CPC .......... *A61B 5/4839* (2013.01); *A61B 5/7275* (2013.01); *A61M 5/1723* (2013.01);
(Continued)

(58) Field of Classification Search
CPC ...... H04N 21/435; H04N 21/44; H04N 19/70; G06N 3/0455; G06N 3/0464
See application file for complete search history.

(56) References Cited

U.S. PATENT DOCUMENTS

| 2014/0016707 A1* | 1/2014 | Wang | H04N 19/31 375/240.26 |
| 2015/0373346 A1* | 12/2015 | Wang | H04N 19/188 375/240.02 |
| 2021/0211733 A1* | 7/2021 | Aksu | H04N 19/46 |

FOREIGN PATENT DOCUMENTS

| WO | WO-2020187587 A1 * | 9/2020 | G06N 3/0454 |
| WO | 2021/140275 A1 | 7/2021 | |
| WO | 2021/209907 A1 | 10/2021 | |

OTHER PUBLICATIONS

"Video Coding For Low Bit Rate Communication", Series H: Audiovisual and Multimedia Systems, Infrastructure of audiovisual services—Coding of moving Video, ITU-T Recommendation H.263, Jan. 2005, 226 pages.

(Continued)

*Primary Examiner* — Sumaiya A Chowdhury
(74) *Attorney, Agent, or Firm* — Joseph C. Drish; Harrington & Smith

(57) ABSTRACT

An example method is provided to include receiving a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying one or more neural networks; decoding the one or more media units; and using the one or more neural networks to enhance or filter one or more frames of the decoded the one or more media units, based on the at least one purpose. An example method includes. Corresponding apparatuses and computer program products are also provided.

22 Claims, 13 Drawing Sheets

(51) Int. Cl.
| | |
|---|---|
| A61M 5/172 | (2006.01) |
| G06N 3/04 | (2023.01) |
| G06N 3/0455 | (2023.01) |
| G16H 20/17 | (2018.01) |
| G16H 50/30 | (2018.01) |
| H04N 19/70 | (2014.01) |
| H04N 21/44 | (2011.01) |

(52) U.S. Cl.
CPC ............. *G06N 3/04* (2013.01); *G06N 3/0455* (2023.01); *G16H 20/17* (2018.01); *G16H 50/30* (2018.01); *H04N 19/70* (2014.11); *H04N 21/435* (2013.01); *H04N 21/44* (2013.01); *A61M 2230/201* (2013.01)

(56) References Cited

OTHER PUBLICATIONS

"Advanced Video Coding For Generic Audiovisual services", Series H: Audiovisual and Multimedia Systems, Infrastructure of audiovisual services—Coding of moving Video, Recommendation ITU-T H.264, Apr. 2017, 812 pages.

"High Efficiency Video Coding", Series H: Audiovisual and Multimedia Systems, Infrastructure of audiovisual services—Coding of moving video, Recommendation ITU-T H.265, Feb. 2018, 692 pages.

"Versatile Video Coding", Series H: Audiovisual and Multimedia Systems Infrastructure of audiovisual services—Coding of moving video, Recommendation ITU-T H.266, Aug. 2020, 516 pages.

"Versatile supplemental enhancement information messages for coded video bitstreams", Series H: Audiovisual and Multimedia Systems Infrastructure of audiovisual services—Coding of moving video, Recommendation ITU-T H.274, Aug. 2020, 86 pages.

"Text of ISO/IEC DIS 15938-17 Compression of Neural Networks for Multimedia Content Description and Analysis", ISO/IEC JTC 1/SC 29/WG 04, N0016, MPEG Video Coding, Oct. 2020, 82 pages.

"Information Technology—Generic Coding of Moving Pictures and Associated Audio Information: Systems", Series H: Audiovisual and Multimedia Systems, Infrastructure of Audiovisual Services—Transmission Multiplexing and Synchronization, Recommendation ITU-T H.222.0, Mar. 2017, 291 pages.

"Information technology—Generic coding of moving pictures and associated audio information: Video", Series H: Audiovisual and Multimedia Systems Infrastructure of audiovisual services—Coding of moving video, ITU-T Recommendation H.262, Feb. 2020, 220 pages.

"Information technology—Universal coded character set (UCS)", ISO/IEC 10646, Sixth edition, Dec. 2020, 9 pages.

"IEEE 802.11", Wikipedia, Retrieved on Feb. 23, 2022, Webpage available at : https://en.wikipedia.org/wiki/IEEE_802.11.

"Information Technology—Coding of Audio-Visual Objects—Part 12: ISO Base Media File Format", ISO/IEC 14496-12, Fifth edition, Dec. 15, 2015, 248 pages.

"Information Technology—Coding of Audio-Visual Objects—Part 15: Advanced Video Coding (AVC) File Format", ISO/IEC 14496-15, First edition, Apr. 15, 2004, 29 pages.

"Information technology—Coded Representation of Immersive Media—Part 5: Video-based Point Cloud Compression", ISO/IEC JTC 1/SC 29/WG 11, ISO/IEC 23090-5, 2019, 102 pages.

"Text of ISO/IEC FDIS 15938-17 Compression of Neural Networks for Multimedia Content Description and Analysis", ISO/IEC JTC 1/SC 29/WG 04, N0080, Apr. 2021, 95 pages.

"Information technology—Multimedia content description interface—Part 17: Compression of neural networks for multimedia content description and analysis", ISO/IEC 15938-17:2020(E), 2020, 89 pages.

Invitation to Pay Additional Search Fees received for corresponding Patent Cooperation Treaty Application No. PCT/IB2022/050955, dated May 9, 2022, 17 pages.

Choi et al., "AHG9/AHG11: SEI message for carriage of neural network information for post filtering", Tencent, Joint Video Experts Team (JVET) of ITU-T SG 16 WP 3 and ISO/IEC JTC 1/SC 29, JVET-U0091-v3, 21st Meeting, Jan. 6-15, 2021, 13 pages.

"Information technology—MPEG Systems Technologies—Part 11: Energy-Efficient Media Consumption (Green Metadata)", ISO/IEC ,JTC1/SC29/WG11, ISO/IEC SoDIS 23001-11/n14597, Apr. 26, 2013, 55 pages.

Onno et al., "Modification of the "quality_layers_info" SEI message to support Virtual Spatial Resolutions", Canon Research Centre France, Joint Video Team (JVT) of ISO/IEC MPEG & ITU-T VCEG (ISO/IEC JTC1/SC29/WG11 and ITU-T SG16 Q.6), JVT-U036, 21st Meeting, Oct. 20-27, 2006, pp. 1-16.

Wang et al., "SE1 manifest and prefix indication SEI messages", Qualcomm Incorporated, Joint Collaborative Team on Video Coding (JCT-VC) of ITU-T SG 16 WP 3 and ISO/IEC JTC 1/SC 29/WG11/JCTVC-AC0025, 29th Meeting, Oct. 19-24, 2017, pp. 1-10.

Bross et al., "Developments in International Video Coding Standardization After AVC, With an Overview of Versatile Video Coding (VVC)", Proceedings of the IEEE, vol. 109, No. 9, Sep. 2021, pp. 1463-1493.

"Working Draft 4 of Compression of neural networks for multimedia content description and analysis", Video Subgroup, ISO/IEC JTC1/SC29/WG11/N19225, Apr. 2020, 48 pages.

He et al., "AHG9: Picture quality metrics SEI message", Qualcomm Incorporated, Joint Video Experts Team (JVET) of ITU-T SG16 WP3 and ISO/IEC JTC 1/SC29/JVET-V0062, 22nd meeting, Apr. 20-28, 2021, 2 pages.

International Search Report and Written Opinion received for corresponding Patent Cooperation Treaty Application No. PCT/IB2022/050955, dated Jun. 30, 2022, 24 pages.

\* cited by examiner

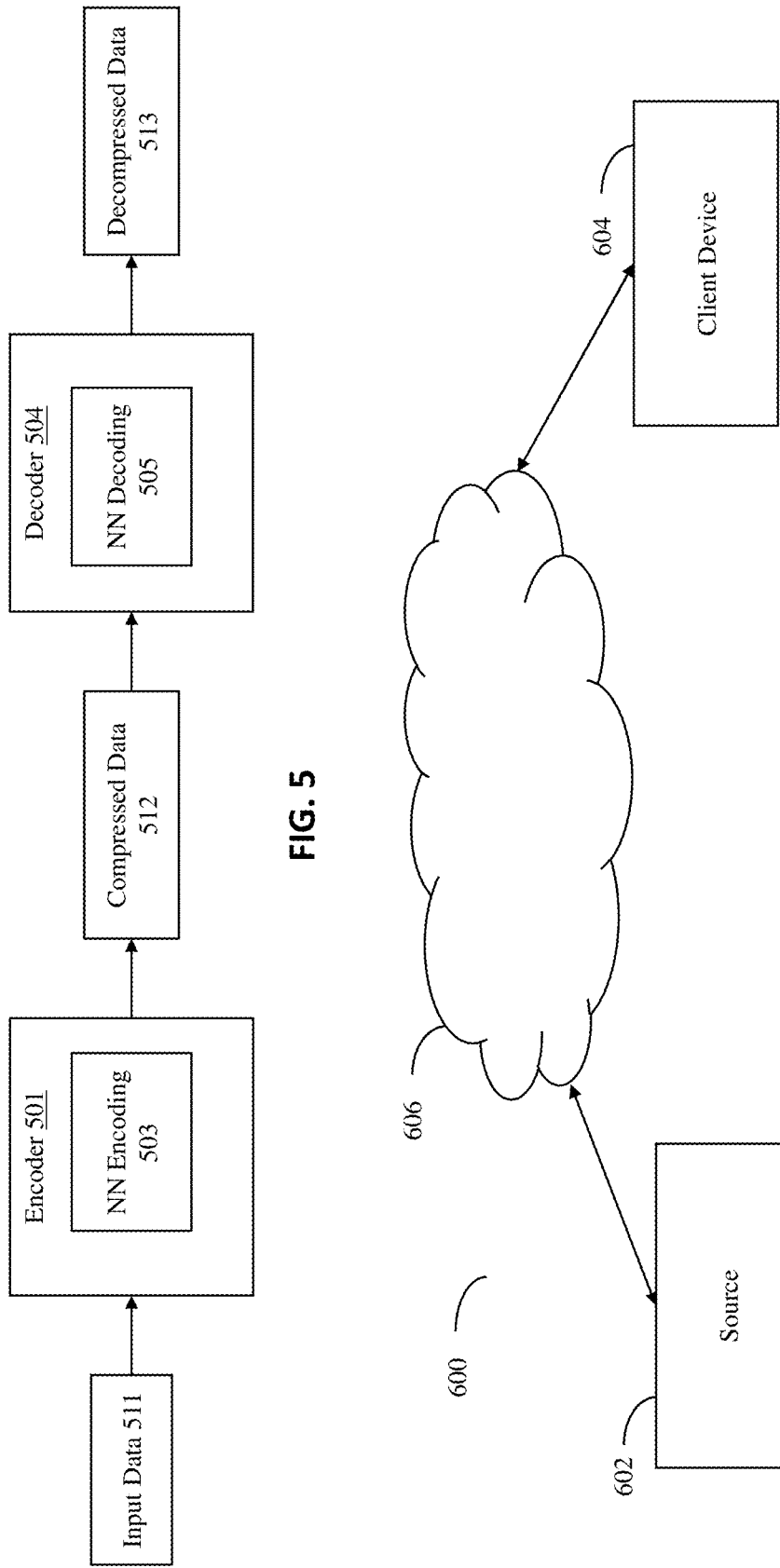

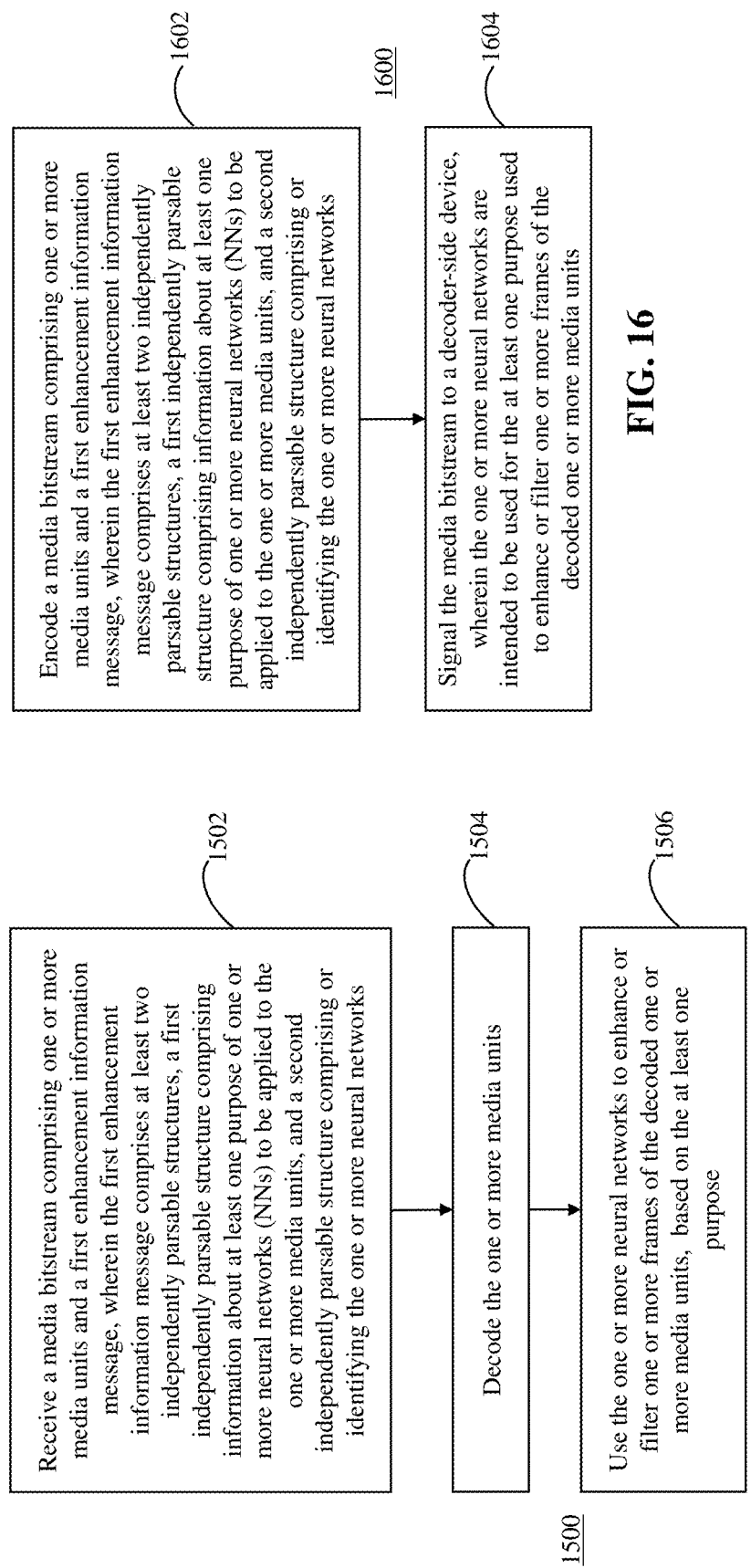

HIGH-LEVEL SYNTAX FOR SIGNALING NEURAL NETWORKS WITHIN A MEDIA BITSTREAM

TECHNICAL FIELD

The examples and non-limiting embodiments relate generally to multimedia transport and neural networks, and more particularly, to a high-level syntax for signaling neural networks within a media bitstream.

BACKGROUND

It is known to provide standardized formats for exchange of neural networks.

SUMMARY

An example method includes receiving a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying the one or more neural networks; decoding the one or more media units; and using the one or more neural networks to enhance or filter one or more frames of the decoded one or more media units, based on the at least one purpose.

The example method of claim may further include receiving a container, wherein the container comprises: a second enhancement information message, wherein the second enhancement information message comprises information for identifying a standard neural network or a separately provided neural network via a reference; and an update to an identified neural network.

The example method may further include updating the identified NN by using the update to the identified neural network; and using the updated identified NN to enhance or filter the one or more frames of the decoded one or more media units.

Another example method includes encoding a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying the one or more neural networks; and signaling the media bitstream to a decoder-side device, wherein the one or more neural networks are intended to be used for the at least one purpose to enhance or filter one or more frames of the decoded one or more media units.

Yet another example method includes encoding a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying the one or more neural networks; and signaling the media bitstream to a decoder-side device, wherein the one or more neural networks are intended to be used by a decoder to enhance or filter one or more frames of the decoded one or more media units based on the at least one purpose.

The example methods may further include, wherein the first enhancement information message comprises a neural network (NN) supplemental enhancement information message.

The example methods may further include, wherein the second independently parsable structure comprises an MPEG neural network representation (NNR) bitstream.

The example methods may further include, wherein the one or more media units comprise one or more video units, and wherein the one or more video units comprise one or more network abstraction layer video units.

The example methods may further include, wherein the one or more of the at least two independently parsable structures comprises supplemental enhancement information messages.

The example methods may further include, wherein a payload of the NN SEI message comprises one or more syntax elements for specifying the at least one purpose of the one or more NNs to be applied to the one or more media units.

The example methods may further include, wherein the one or more of the at least two independently parsable structures comprises one or more syntax elements at a pre-defined order in association with to the supplemental enhancement information messages.

The example methods may further include, wherein the enhancement information message further comprises a gain enhancement information message, wherein the gain enhancement information message specifies an expected gain achieved when the one or more NNs are applied.

The example methods may further include, wherein the first enhancement information message further comprises a topology enhancement information message, and wherein the topology enhancement information message specifies a subset of topology for performing the at least one purpose specified in the enhancement information message.

The example methods may further include, wherein the first enhancement information message further comprises a scope enhancement information message for specifying a scope within which an enhancement or filter is valid.

The example methods may further include defining a container, wherein the container includes: an identifier for identifying a NN of the one or more NNs; and a filter activation enhancement information message for activating a temporal scope, a spatial scope, or a spatio-temporal scope.

The example methods may further include, wherein the first enhancement information message further comprises information for indicating which of the at least two independent parsable structures are mandatory to be processed in order to perform the enhancement or filtering.

The example methods may further include, wherein the scope pertains valid from a position of an enhancement information container structure until a specific event appears in the media bitstream.

The example methods may further include, wherein the second independently parsable structure identifies the one or more neural networks to be a pre-defined NN, and using the one or more NNs comprises using the pre-defined NN to enhance or filter the one or more frames of the decoded one or more media units.

The example methods may further include, wherein the second independently parsable structure identifies the one or more neural networks to be a pre-defined NN, and wherein the pre-defined NN is used to enhance or filter the one or more frames of the decoded one or more media units.

The example methods may further include defining a container, wherein the container comprises includes: a second enhancement information message, and wherein the second enhancement information message further comprises information for identifying a standard neural network or a separately provided neural network via a reference; and an update to the identified neural network.

The example methods may further include defining a container, wherein the update to the neural network is represented by a neural network representation bitstream, for example, an MPEG neural network representation bitstream, an ISO/IEC 15938-17 bitstream, or an MPEG neural network representation (ISO/IEC 15938-17) bitstream.

The example methods may further include updating a NN identified by the second independently parsable structure, wherein the updated NN is used to enhance or filter the one or more frames of the decoded one or more media units.

The example methods may further include, wherein a decoder-side device comprises a set of topologies of the one or more NNs, and wherein a topology comprises an architecture of NN comprising at least one of a number of layers, types of layers, a number of computational units per layer, a number of convolutional channels per layer, or hyper-parameters of the layers.

The example methods may further include, wherein the first enhancement information further comprises information about a topology from a set of topologies to be used to enhance or filter the one or more frames of the decoded one or more media units.

The example methods may further include, wherein the first enhancement information comprises a unique identifier (ID) for identifying the topology.

The example methods may further include, wherein the first enhancement information comprises a representation of a neural network topology to be used to enhance or filter the one or more frames of the decoded one or more media units.

The example methods may further include decoding the NNR bitstream to extract the decoded one or more NNs.

The example methods may further include, wherein the media bitstream or the first enhancement information message further includes a scaling factor flag message, and wherein the scaling factor flag message indicates whether an output of the one or more NNs need to be scaled.

The example methods may further include, wherein the scaling factor flag message includes one or more values to be used to scale the output of the one or more NNs.

The example methods may further include, wherein the media bitstream or the first enhancement information message further includes a scaling factor message, and wherein the scaling factor message comprises one or more values to be used to scale the output of the one or more NNs The example methods may further include, wherein the media bitstream or the first enhancement information message further includes a residual filtering flag message, and wherein the residual filtering flag message indicates whether the output of the one or more NNs is to be added to an input of the one or more NNs.

The example methods may further include, wherein the media bitstream or the first enhancement information message further includes a normalization flag message, and wherein the normalization flag message indicates a normalization mode to be applied to the one or more frames that are input to the one or more NNs.

The example methods may further include, wherein the normalization flag message includes normalizing values to be used in order to normalize the one or more frames that are input to the one or more NNs.

The example methods may further include, wherein the media bitstream or the first enhancement information message further includes a normalization message, and wherein the normalization message includes normalizing values to be used in order to normalize the one or more frames that are input to the one or more NNs The example methods may further include, wherein the media comprises at least one of a video, an image, or audio.

A yet another example method includes receiving an independently parsable structure comprising or identifying one or more neural networks (NNs); receiving a media bitstream comprising the independently parsable structure natively or logically; obtaining the one or more NNs by using the independently parsable structure; and decoding one or more media frames of the media bitstream by using the obtained one or more NNs.

A still another example method includes encoding a media bitstream comprising one or more media frames and an independently parsable structure comprising or identifying one or more neural networks (NNs); and signaling the media bitstream comprising the independently parsable structure natively or logically to a decoder-side device, wherein the one or more NNs are obtained by using the independently parsable structure, and wherein the one or more media frames of the media bitstream are decoded by using the obtained one or more NNs.

The example methods may further include, wherein the media bitstream comprises network abstraction layer (NAL) units.

The example methods may further include, wherein the independently parsable structure comprises a non video coding layer (non-VCL) NAL unit.

The example methods may further include, wherein the one or more neural networks comprise one or more pre-defined NNs, and wherein the independently parsable structure identifies that the one or more NNs comprise one or more pre-defined NNs, and wherein decoding the one or more media frames of the media bitstream comprises using the one or more pre-defined NNs to decode the one or more media frames of the media bitstream.

The example methods may further include, wherein the one or more neural networks comprise one or more pre-defined NNs, and wherein the independently parsable structure identifies that the one or more NNs comprise one or more pre-defined NNs, and wherein the one or more pre-defined NNs are used to decode the one or more media frames of the media bitstream.

The example methods may further include updating the one or more pre-defined NNs and using the updated one or more pre-defined NNs to decode the one or more media frames of the media bitstream.

The example methods may further include updating the one or more pre-defined NNs, wherein the updated one or more pre-defined NNs are used to decode the one or more media frames of the media bitstream.

The example methods may further include updating the one or more NNs and using the updated NNs to decode the one or more media frames of the media bitstream.

The example methods may further include updating the one or more NNs and wherein the updated NNs are used to decode the one or more media frames of the media bitstream.

The example methods may further include, wherein one or more parameter sets comprise the independently parsable structure.

The example methods may further include defining one or more adaptation parameter sets for the media bitstream, wherein the one or more adaptation parameter sets comprise the independently parsable structure, and wherein an adaptation parameter type indicates a neural network filtering.

The example methods may further include, wherein the one or more adaptation parameter sets comprises one or more identities (IDs), and wherein an ID enables using an NN signaled in an adaptation parameter set, by signaling the ID of the adaptation parameter set in a slice header or a picture header.

A still another example method includes encoding a media bitstream including one or more media frames; obtaining one or more neural networks (NNs); encoding an independently parsable structure including or identifying the one or more NNs, wherein the media bitstream comprises the independently parsable structure natively or logically; and reconstructing one or more media frames encoded into the media bitstream by using the one or more NNs.

The method may further include using the one or more reconstructed media frames as a source for predicting other media frames.

An example apparatus includes at least one processor; and at least one memory including computer program code, which when executed by the at least one processor, causes the apparatus to: receive a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying the one or more neural networks; decode the one or more media units; and use the one or more neural networks to enhance or filter one or more frames of the decoded one or more media units, based on the at least one purpose.

The example apparatus may be further caused to perform the one or more of the example methods described in previous paragraphs.

Another example apparatus includes at least one processor; and at least one memory including computer program code, which when executed by the at least one processor, causes the apparatus to: encode a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying one or more neural networks; and signal the media bitstream to a decoder-side device, wherein the one or more neural networks are intended to be used for the at least one purpose to enhance or filter one or more frames of the decoded one or more media units.

The example apparatus may be further caused to perform the one or more of the example methods described in previous paragraphs.

A yet another example apparatus includes at least one processor; and at least one memory including computer program code, which when executed by the at least one processor, causes the apparatus to: receive an independently parsable structure comprising or identifying one or more neural networks (NNs); receive a media bitstream comprising the independently parsable structure natively or logically; obtain the one or more NNs by using the independently parsable structure; and decode one or more media frames of the media bitstream by using the obtained one or more NNs.

The example apparatus may be further caused to perform the one or more of the example methods described in previous paragraphs.

A still another example apparatus includes at least one processor; and at least one memory including computer program code, which when executed by the at least one processor, causes the apparatus to: encode a media bitstream comprising one or more media frames and an independently parsable structure comprising or identifying one or more neural networks (NNs); and signal the media bitstream comprising the independently parsable structure natively or logically to a decoder-side device, wherein the one or more NNs are obtained by using the independently parsable structure, and wherein the one or more media frames of the media bitstream are decoded by using the obtained one or more NNs.

The example apparatus may be further caused to perform the one or more of the example methods described in previous paragraphs.

A still another example apparatus includes at least one processor; and at least one memory including computer program code, which when executed by the at least one processor, causes the apparatus to: encode a media bitstream includes one or more media frames; obtain one or more neural networks (NNs); encode an independently parsable structure includes or identifying the one or more NNs, wherein the media bitstream comprises the independently parsable structure natively or logically; and reconstruct one or more media frames encoded into the media bitstream by using the one or more NNs.

The example apparatus may be further caused to use the one or more reconstructed media frames as a source for predicting other media frames.

An example computer readable medium includes program instructions for performing at least the following: encode a media bitstream comprising one or more media units and a first enhancement information message, wherein the first enhancement information message comprises at least two independently parsable structures, a first independently parsable structure comprising information about at least one purpose of one or more neural networks (NNs) to be applied to the one or more media units, and a second independently parsable structure comprising or identifying one or more neural networks; and signal the media bitstream to a decoder-side device, wherein the one or more neural networks are intended to be used for the at least one purpose to enhance or filter one or more frames of the decoded one or more media units.

The example computer readable medium may further include, wherein the computer readable comprises a non-transitory computer readable medium.

Another example computer readable medium includes program instructions for performing at least the following: receive an independently parsable structure comprising or identifying one or more neural networks (NNs); receive a media bitstream comprising the independently parsable structure natively or logically; obtain the one or more NNs by using the independently parsable structure; and decode one or more media frames of the media bitstream by using the obtained one or more NNs.

The example computer readable medium may further include, wherein the computer readable comprises a non-transitory computer readable medium.

Yet another computer readable medium includes program instructions for performing at least the following: encode a media bitstream comprising one or more media frames and an independently parsable structure comprising or identifying one or more neural networks (NNs); and signal the media bitstream comprising the independently parsable structure natively or logically to a decoder-side device, wherein the one or more NNs are obtained by using the independently parsable structure, and wherein the one or more media frames of the media bitstream are decoded by using the obtained one or more NNs.

The example computer readable medium may further include, wherein the computer readable comprises a non-transitory computer readable medium.

BRIEF DESCRIPTION OF THE DRAWINGS

The foregoing aspects and other features are explained in the following description, taken in connection with the accompanying drawings, wherein:

FIG. 5 is a block diagram showing an interface between an encoder and a decoder in accordance with the examples described herein.

FIG. 6 illustrates a system configured to support streaming of media data from a source to a client device.

FIG. 15 is an example method to receive neural networks within a media bitstream, in accordance with an example embodiment.

FIG. 16 is another example method to signal neural networks within a media bitstream, in accordance with another example embodiment.

DETAILED DESCRIPTION OF EXAMPLE EMBODIMENTS

Figure 2:
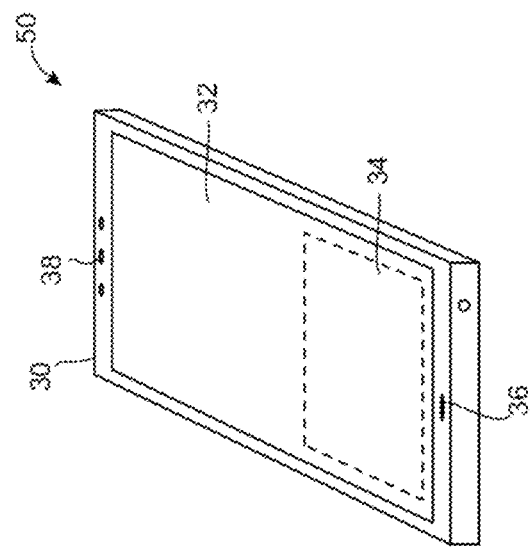
FIG. 2 shows schematically a user equipment suitable for employing embodiments of the examples described herein.

The following acronyms and abbreviations that may be found in the specification and/or the drawing figures are defined as follows:

3GP 3GPP file format
3GPP 3rd Generation Partnership Project
3GPP TS 3GPP technical specification
4CC four character code
4G fourth generation of broadband cellular network technology
5G fifth generation cellular network technology
5GC 5G core network
ACC accuracy
AI artificial intelligence
AIoT AI-enabled IoT
a.k.a. also known as
AMF access and mobility management function
AVC advanced video coding
CABAC context-adaptive binary arithmetic coding
CDMA code-division multiple access
CE core experiment
CU central unit
DASH dynamic adaptive streaming over HTTP
DCT discrete cosine transform
DSP digital signal processor
DU distributed unit
eNB (or eNodeB) evolved Node B (for example, an LTE base station)
EN-DC E-UTRA-NR dual connectivity
en-gNB or En-gNB node providing NR user plane and control plane protocol terminations towards the UE, and acting as secondary node in EN-DC
E-UTRA evolved universal terrestrial radio access, for example, the LTE radio access technology
FDMA frequency division multiple access
f(n) fixed-pattern bit string using n bits written (from left to right) with the left bit first.
F1 or F1-C interface between CU and DU control interface
gNB (or gNodeB) base station for 5G/NR, for example, a node providing NR user plane and control plane protocol terminations towards the UE, and connected via the NG interface to the 5GC
GSM Global System for Mobile communications
H.222.0 MPEG-2 Systems is formally known as ISO/IEC 13818-1 and as ITU-T Rec. H.222.0
H.26x family of video coding standards in the domain of the ITU-T
HLS high level syntax
IBC intra block copy
ID identifier
IEC International Electrotechnical Commission
IEEE Institute of Electrical and Electronics Engineers
I/F interface
IMD integrated messaging device
IMS instant messaging service
IoT internet of things
IP internet protocol
ISO International Organization for Standardization
ISOBMFF ISO base media file format
ITU International Telecommunication Union
ITU-T ITU Telecommunication Standardization Sector
LTE long-term evolution
LZMA Lempel-Ziv-Markov chain compression LZMA2 simple container format that can include both uncompressed data and LZMA data
LZO Lempel-Ziv-Oberhumer compression
LZW Lempel-Ziv-Welch compression
MAC medium access control
mdat MediaDataBox
MME mobility management entity
MMS multimedia messaging service
moov MovieBox
MP4 file format for MPEG-4 Part 14 files
MPEG moving picture experts group
MPEG-2 H.222/H.262 as defined by the ITU
MPEG-4 audio and video coding standard for ISO/IEC 14496
MSB most significant bit
NAL network abstraction layer
NDU NN compressed data unit
ng or NG new generation
ng-eNB or NG-eNB new generation eNB
NN neural network
NNEF neural network exchange format
NNR neural network representation
NR new radio (5G radio)
N/W or NW network
ONNX Open Neural Network eXchange
PB protocol buffers
PC personal computer
PDA personal digital assistant
PDCP packet data convergence protocol
PHY physical layer
PID packet identifier
PLC power line communication
PSNR peak signal-to-noise ratio
RAM random access memory
RAN radio access network
RFC request for comments
RFID radio frequency identification
RLC radio link control
RRC radio resource control
RRH remote radio head
RU radio unit
Rx receiver
SDAP service data adaptation protocol
SGW serving gateway
SMF session management function
SMS short messaging service
st(v) null-terminated string encoded as UTF-8 characters as specified in ISO/IEC 10646
SVC scalable video coding
S1 interface between eNodeBs and the EPC
TCP-IP transmission control protocol-internet protocol
TDMA time divisional multiple access
trak TrackBox
TS transport stream
TV television
Tx transmitter
UE user equipment
ue(v) unsigned integer Exp-Golomb-coded syntax element with the left bit first
UICC Universal Integrated Circuit Card
UMTS Universal Mobile Telecommunications System
u(n) unsigned integer using n bits
UPF user plane function
URI uniform resource identifier
URL uniform resource locator
UTF-8 8-bit Unicode Transformation Format
WLAN wireless local area network
X2 interconnecting interface between two eNodeBs in LTE network
Xn interface between two NG-RAN nodes Some embodiments will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms 'data,' 'content,' 'information,' and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network device, other network device, and/or other computing device.

As defined herein, a 'computer-readable storage medium,' which refers to a non-transitory physical storage medium (e.g., volatile or non-volatile memory device), can be differentiated from a 'computer-readable transmission medium,' which refers to an electromagnetic signal.

A method, apparatus and computer program product are provided in accordance with an example embodiment in order to provide signaling of neural networks within a media bitstream.

Figure 1:
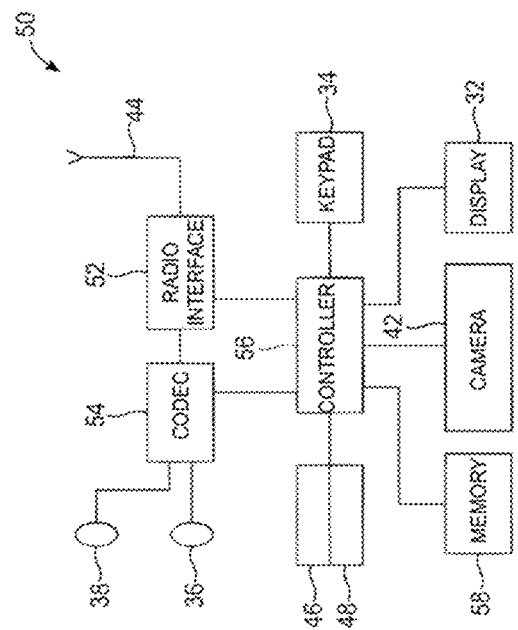
FIG. 1 shows schematically an electronic device employing embodiments of the examples described herein.

The following describes in detail suitable apparatus and possible mechanisms for signaling neural networks within an encoded media bitstream according to embodiments. In this regard reference is first made to FIG. 1 and FIG. 2, where FIG. 1 shows an example block diagram of an apparatus 50. The apparatus may be an Internet of Things (IoT) apparatus configured to perform various functions, for example, gathering information by one or more sensors, receiving or transmitting information, analyzing information gathered or received by the apparatus, or the like. The apparatus may comprise a video coding system, which may incorporate a codec. FIG. 2 shows a layout of an apparatus according to an example embodiment. The elements of FIG. 1 and FIG. 2 will be explained next.

The electronic device 50 may for example be a mobile terminal or user equipment of a wireless communication system, a sensor device, a tag, or a lower power device. However, it would be appreciated that embodiments of the examples described herein may be implemented within any electronic device or apparatus which may process data by neural networks.

The apparatus 50 may comprise a housing 30 for incorporating and protecting the device. The apparatus 50 may further comprise a display 32, for example, in the form of a liquid crystal display, light emitting diode display, organic light emitting diode display, and the like. In other embodiments of the examples described herein the display may be any suitable display technology suitable to display media or multimedia content, for example, an image or a video. The apparatus 50 may further comprise a keypad 34. In other embodiments of the examples described herein any suitable data or user interface mechanism may be employed. For example the user interface may be implemented as a virtual keyboard or data entry system as part of a touch-sensitive display.

The apparatus may comprise a microphone 36 or any suitable audio input which may be a digital or analogue signal input. The apparatus 50 may further comprise an audio output device which in embodiments of the examples described herein may be any one of: an earpiece 38, speaker, or an analogue audio or digital audio output connection. The apparatus 50 may also comprise a battery (or in other embodiments of the examples described herein the device may be powered by any suitable mobile energy device such as solar cell, fuel cell or clockwork generator). The apparatus may further comprise a camera capable of recording or capturing images and/or video. The apparatus 50 may further comprise an infrared port for short range line of sight communication to other devices. In other embodiments the apparatus 50 may further comprise any suitable short range communication solution such as for example a Bluetooth® wireless connection or a USB/firewire wired connection.

The apparatus 50 may comprise a controller 56, a processor or a processor circuitry for controlling the apparatus 50. The controller 56 may be connected to a memory 58 which in embodiments of the examples described herein may store both data in the form of an image, audio data, video data and/or may also store instructions for implementation on the controller 56. The controller 56 may further be connected to codec circuitry 54 suitable for carrying out coding and/or decoding of audio, image and/or video data or assisting in coding and/or decoding carried out by the controller.

The apparatus 50 may further comprise a card reader 48 and a smart card 46, for example, a UICC and UICC reader for providing user information and being suitable for providing authentication information for authentication and authorization of the user at a network.

The apparatus 50 may comprise radio interface circuitry 52 connected to the controller and suitable for generating wireless communication signals for example for communication with a cellular communications network, a wireless communications system or a wireless local area network. The apparatus 50 may further comprise an antenna 44 connected to the radio interface circuitry 52 for transmitting radio frequency signals generated at the radio interface circuitry 52 to other apparatus(es) and/or for receiving radio frequency signals from other apparatus(es).

The apparatus 50 may comprise a camera 42 capable of recording or detecting individual frames which are then passed to the codec 54 or the controller for processing. The apparatus may receive the video image data for processing from another device prior to transmission and/or storage. The apparatus 50 may also receive either wirelessly or by a wired connection the image for coding/decoding. The structural elements of apparatus 50 described above represent examples of means for performing a corresponding function.

Figure 3:
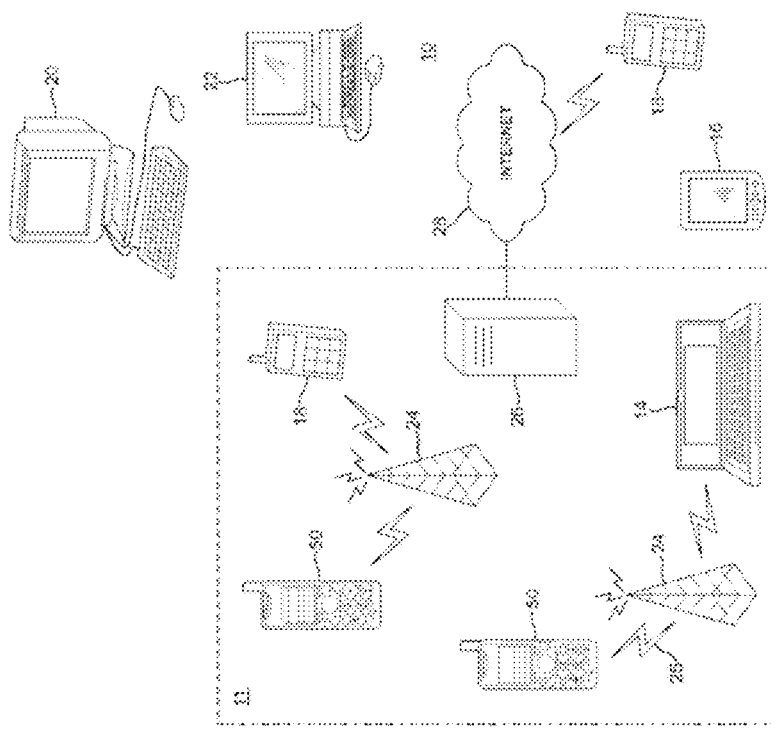
FIG. 3 further shows schematically electronic devices employing embodiments of the examples described herein connected using wireless and wired network connections.

With respect to FIG. 3, an example of a system within which embodiments of the examples described herein can be utilized is shown. The system 10 comprises multiple communication devices which can communicate through one or more networks. The system 10 may comprise any combination of wired or wireless networks including, but not limited to a wireless cellular telephone network (such as a GSM, UMTS, CDMA, LTE, 4G, 5G network, and the like), a wireless local area network (WLAN) such as defined by any of the IEEE 802.x standards, a Bluetooth® personal area network, an Ethernet local area network, a token ring local area network, a wide area network, and the Internet.

The system 10 may include both wired and wireless communication devices and/or apparatus 50 suitable for implementing embodiments of the examples described herein.

For example, the system shown in FIG. 3 shows a mobile telephone network 11 and a representation of the Internet 28. Connectivity to the Internet 28 may include, but is not limited to, long range wireless connections, short range wireless connections, and various wired connections including, but not limited to, telephone lines, cable lines, power lines, and similar communication pathways.

The example communication devices shown in the system 10 may include, but are not limited to, an electronic device or apparatus 50, a combination of a personal digital assistant (PDA) and a mobile telephone 14, a PDA 16, an integrated messaging device (IMD) 18, a desktop computer 20, a notebook computer 22. The apparatus 50 may be stationary or mobile when carried by an individual who is moving. The apparatus 50 may also be located in a mode of transport including, but not limited to, a car, a truck, a taxi, a bus, a train, a boat, an airplane, a bicycle, a motorcycle or any similar suitable mode of transport.

The embodiments may also be implemented in a set-top box; for example, a digital TV receiver, which may/may not have a display or wireless capabilities, in tablets or (laptop) personal computers (PC), which have hardware and/or software to process neural network data, in various operating systems, and in chipsets, processors, DSPs and/or embedded systems offering hardware/software based coding.

Some or further apparatus may send and receive calls and messages and communicate with service providers through a wireless connection 25 to a base station 24. The base station 24 may be connected to a network server 26 that allows communication between the mobile telephone network 11 and the internet 28. The system may include additional communication devices and communication devices of various types.

The communication devices may communicate using various transmission technologies including, but not limited to, code division multiple access (CDMA), global systems for mobile communications (GSM), universal mobile telecommunications system (UMTS), time divisional multiple access (TDMA), frequency division multiple access (FDMA), transmission control protocol-internet protocol (TCP-IP), short messaging service (SMS), multimedia messaging service (MMS), email, instant messaging service (IMS), Bluetooth®, IEEE 802.11, 3GPP Narrowband IoT and any similar wireless communication technology. A communications device involved in implementing various embodiments of the examples described herein may communicate using various media including, but not limited to, radio, infrared, laser, cable connections, and any suitable connection.

In telecommunications and data networks, a channel may refer either to a physical channel or to a logical channel. A physical channel may refer to a physical transmission medium such as a wire, whereas a logical channel may refer to a logical connection over a multiplexed medium, capable of conveying several logical channels. A channel may be used for conveying an information signal, for example a bitstream, from one or several senders (or transmitters) to one or several receivers.

The embodiments may also be implemented in so-called internet of things (IoT) devices. The IoT may be defined, for example, as an interconnection of uniquely identifiable embedded computing devices within the existing Internet infrastructure. The convergence of various technologies has and may enable many fields of embedded systems, such as wireless sensor networks, control systems, home/building automation, and the like, to be included the Internet of Things (IoT). In order to utilize the Internet, the IoT devices are provided with an IP address as a unique identifier. The IoT devices may be provided with a radio transmitter, such as WLAN or Bluetooth® transmitter or an RFID tag. Alternatively, IoT devices may have access to an IP-based network via a wired network, such as an Ethernet-based network or a power-line connection (PLC).

The devices/system described in FIGS. 1 to 3 may be used for encoding, decoding, and/or transporting, for example, neural network representation and/or media stream.

An MPEG-2 transport stream (TS), specified in ISO/IEC 13818-1 or equivalently in ITU-T Recommendation H.222.0, is a format for carrying audio, video, and other media as well as program metadata or other metadata, in a multiplexed stream. A packet identifier (PID) is used to identify an elementary stream (a.k.a. packetized elementary stream) within the TS. Hence, a logical channel within an MPEG-2 TS may be considered to correspond to a specific PID value.

Available media file format standards include ISO base media file format (ISO/IEC 14496-12, which may be abbreviated ISOBMFF) and file format for NAL unit structured video (ISO/IEC 14496-15), which derives from the ISOBMFF.

Video codec consists of an encoder that transforms the input video into a compressed representation suited for storage/transmission and a decoder that can decompress the compressed video representation back into a viewable form. A video encoder and/or a video decoder may also be separate from each other, for example, need not form a codec. Typically, encoder discards some information in the original video sequence in order to represent the video in a more compact form (e.g., at a lower bitrate).

Typical hybrid video encoders, for example, many encoder implementations of ITU-T H.263 and H.264, encode the video information in two phases. Firstly pixel values in a certain picture area (or 'block') are predicted, for example, by motion compensation means (finding and indicating an area in one of the previously coded video frames that corresponds closely to the block being coded) or by spatial means (using the pixel values around the block to be coded in a specified manner). Secondly the prediction error, for example, the difference between the predicted block of pixels and the original block of pixels, is coded. This is typically done by transforming the difference in pixel values using a specified transform (for example, Discrete Cosine Transform (DCT) or a variant of it), quantizing the coefficients and entropy coding the quantized coefficients. By varying the fidelity of the quantization process, encoder can control the balance between the accuracy of the pixel representation (picture quality) and size of the resulting coded video representation (file size or transmission bitrate).

In temporal prediction, the sources of prediction are previously decoded pictures (a.k.a. reference pictures). In intra block copy (IBC; a.k.a. intra-block-copy prediction and current picture referencing), prediction is applied similarly to temporal prediction, but the reference picture is the current picture and only previously decoded samples can be referred in the prediction process. Inter-layer or inter-view prediction may be applied similarly to temporal prediction, but the reference picture is a decoded picture from another scalable layer or from another view, respectively. In some cases, inter prediction may refer to temporal prediction only, while in other cases inter prediction may refer collectively to temporal prediction and any of intra block copy, inter-layer prediction, and inter-view prediction provided that they are performed with the same or similar process than temporal prediction. Inter prediction or temporal prediction may sometimes be referred to as motion compensation or motion-compensated prediction.

Inter prediction, which may also be referred to as temporal prediction, motion compensation, or motion-compensated prediction, reduces temporal redundancy. In inter prediction the sources of prediction are previously decoded pictures. Intra prediction utilizes the fact that adjacent pixels within the same picture are likely to be correlated. Intra prediction can be performed in spatial or transform domain, for example, either sample values or transform coefficients can be predicted. Intra prediction is typically exploited in intra coding, where no inter prediction is applied.

One outcome of the coding procedure is a set of coding parameters, such as motion vectors and quantized transform coefficients. Many parameters can be entropy-coded more efficiently when they are predicted first from spatially or temporally neighboring parameters. For example, a motion vector may be predicted from spatially adjacent motion vectors and only the difference relative to the motion vector predictor may be coded. Prediction of coding parameters and intra prediction may be collectively referred to as in-picture prediction.

Figure 4:
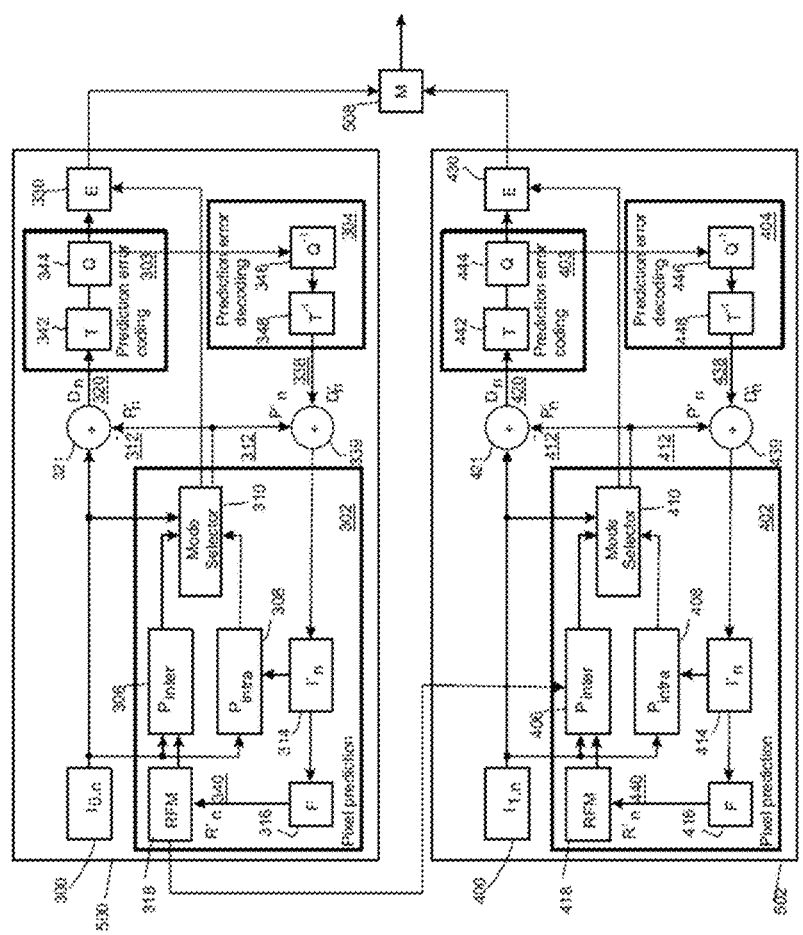
FIG. 4 shows schematically a block diagram of an encoder on a general level.

FIG. 4 shows a block diagram of a general structure of a video encoder. FIG. 4 presents an encoder for two layers, but it would be appreciated that presented encoder could be similarly extended to encode more than two layers. FIG. 4 illustrates a video encoder comprising a first encoder section 500 for a base layer and a second encoder section 502 for an enhancement layer. Each of the first encoder section 500 and the second encoder section 502 may comprise similar elements for encoding incoming pictures. The encoder sections 500, 502 may comprise a pixel predictor 302, 402, prediction error encoder 303, 403 and prediction error decoder 304, 404. FIG. 4 also shows an embodiment of the pixel predictor 302, 402 as comprising an inter-predictor 306, 406, an intra-predictor 308, 408, a mode selector 310, 410, a filter 316, 416, and a reference frame memory 318, 418. The pixel predictor 302 of the first encoder section 500 receives base layer image(s) 300 of a video stream to be encoded at both the inter-predictor 306 (which determines the difference between the image and a motion compensated reference frame) and the intra-predictor 308 (which determines a prediction for an image block based only on the already processed parts of current frame or picture). The output of both the inter-predictor and the intra-predictor are passed to the mode selector 310. The intra-predictor 308 may have more than one intra-prediction modes. Hence, each mode may perform the intra-prediction and provide the predicted signal to the mode selector 310. The mode selector 310 also receives a copy of the base layer image 300. Correspondingly, the pixel predictor 402 of the second encoder section 502 receives enhancement layer image(s) 400 of a video stream to be encoded at both the inter-predictor 406 (which determines the difference between the image and a motion compensated reference frame 418) and the intra-predictor 408 (which determines a prediction for an image block based only on the already processed parts of current frame or picture). The output of both the inter-predictor and the intra-predictor are passed to the mode selector 410. The intra-predictor 408 may have more than one intra-prediction modes. Hence, each mode may perform the intra-prediction and provide the predicted signal to the mode selector 410. The mode selector 410 also receives a copy of the enhancement layer picture 400.

Depending on which encoding mode is selected to encode the current block, the output of the inter-predictor 306, 406 or the output of one of the optional intra-predictor modes or the output of a surface encoder within the mode selector is passed to the output of the mode selector 310, 410. The output of the mode selector 310, 410 is passed to a first summing device 321, 421. The first summing device may subtract the output of the pixel predictor 302, 402 from the base layer image 300 or the enhancement layer image 400 to produce a first prediction error signal 320, 420 which is input to the prediction error encoder 303, 403.

The pixel predictor 302, 402 further receives from a preliminary reconstructor 339, 439 the combination of the prediction representation of the image block 312, 412 and the output 338, 438 of the prediction error decoder 304, 404. The preliminary reconstructed image 314, 414 may be passed to the intra-predictor 308, 408 and to a filter 316, 416. The filter 316, 416 receiving the preliminary representation may filter the preliminary representation and output a final reconstructed image 340, 440 which may be saved in a reference frame memory 318, 418. The reference frame memory 318 may be connected to the inter-predictor 306 to be used as the reference image against which a future base layer image 300 is compared in inter-prediction operations. Subject to the base layer being selected and indicated to be source for inter-layer sample prediction and/or inter-layer motion information prediction of the enhancement layer according to some embodiments, the reference frame memory 318 may also be connected to the inter-predictor 406 to be used as the reference image against which a future enhancement layer image 400 is compared in inter-prediction operations. Moreover, the reference frame memory 418 may be connected to the inter-predictor 406 to be used as the reference image against which a future enhancement layer image 400 is compared in inter-prediction operations.

Filtering parameters from the filter 316 of the first encoder section 500 may be provided to the second encoder section 502 subject to the base layer being selected and indicated to be source for predicting the filtering parameters of the enhancement layer according to some embodiments.

The prediction error encoder 303, 403 comprises a transform unit 342, 442 and a quantizer 344, 444. The transform unit 342, 442 transforms the first prediction error signal 320, 420 to a transform domain. The transform is, for example, the DCT transform. The quantizer 344, 444 quantizes the transform domain signal, for example, the DCT coefficients, to form quantized coefficients.

The prediction error decoder 304, 404 receives the output from the prediction error encoder 303, 403 and performs the opposite processes of the prediction error encoder 303, 403 to produce a decoded prediction error signal 338, 438 which, when combined with the prediction representation of the image block 312, 412 at the second summing device 339, 439, produces the preliminary reconstructed image 314, 414. The prediction error decoder may be considered to comprise a dequantizer 346, 446, which dequantizes the quantized coefficient values, for example, DCT coefficients, to reconstruct the transform signal and an inverse transformation unit 348, 448, which performs the inverse transformation to the reconstructed transform signal wherein the output of the inverse transformation unit 348, 448 contains reconstructed block(s). The prediction error decoder may also comprise a block filter which may filter the reconstructed block(s) according to further decoded information and filter parameters.

The entropy encoder 330, 430 receives the output of the prediction error encoder 303, 403 and may perform a suitable entropy encoding/variable length encoding on the signal to provide error detection and correction capability. The outputs of the entropy encoders 330, 430 may be inserted into a bitstream, for example, by a multiplexer 508.

FIG. 5 is a block diagram showing the interface between an encoder 501 implementing neural network encoding 503, and a decoder 504 implementing neural network decoding 505 in accordance with the examples described herein. The encoder 501 may embody a device, a software method or a hardware circuit. The encoder 501 has the goal of compressing input data 511 (for example, an input video) to compressed data 512 (for example, a bitstream) such that the bitrate is minimized, and the accuracy of an analysis or processing algorithm is maximized. To this end, the encoder 501 uses an encoder or compression algorithm, for example, to perform neural network encoding 503.

The general analysis or processing algorithm may be part of the decoder 504. The decoder 504 uses a decoder or decompression algorithm, for example, to perform the neural network decoding 505 to decode the compressed data 512 (for example, compressed video) which was encoded by the encoder 501. The decoder 504 produces decompressed data 513 (for example, reconstructed data).

The encoder 501 and decoder 504 may be entities implementing an abstraction, may be separate entities or the same entities, or may be part of the same physical device.

The analysis/processing algorithm may be any algorithm, traditional or learned from data. In the case of an algorithm which is learned from data, it is assumed that this algorithm can be modified or updated, for example, by using optimization via gradient descent. One example of the learned algorithm is a neural network.

The method and apparatus of an example embodiment may be utilized in a wide variety of systems, including systems that rely upon the compression and decompression of media data and possibly also the associated metadata. In one embodiment, however, the method and apparatus are configured to compress the media data and associated metadata streamed from a source via a content delivery network to a client device, at which point the compressed media data and associated metadata is decompressed or otherwise processed. In this regard, FIG. 6 depicts an example of such a system 600 that includes a source 602 of media data and associated metadata. The source may be, in one embodiment, a server. However, the source may be embodied in other manners if so desired. The source is configured to stream the media data and associated metadata to the client device 604. The client device may be embodied by a media player, a multimedia system, a video system, a smart phone, a mobile telephone or other user equipment, a personal computer, a tablet computer or any other computing device configured to receive and decompress the media data and process associated metadata. In the illustrated embodiment, boxes of media data and boxes of metadata are streamed via a network 606, such as any of a wide variety of types of wireless networks and/or wireline networks. The client device is configured to receive structured information containing media, metadata and any other relevant representation of information containing the media and the metadata and to decompress the media data and process the associated metadata (e.g. for proper playback timing of decompressed media data).

Figure 7:
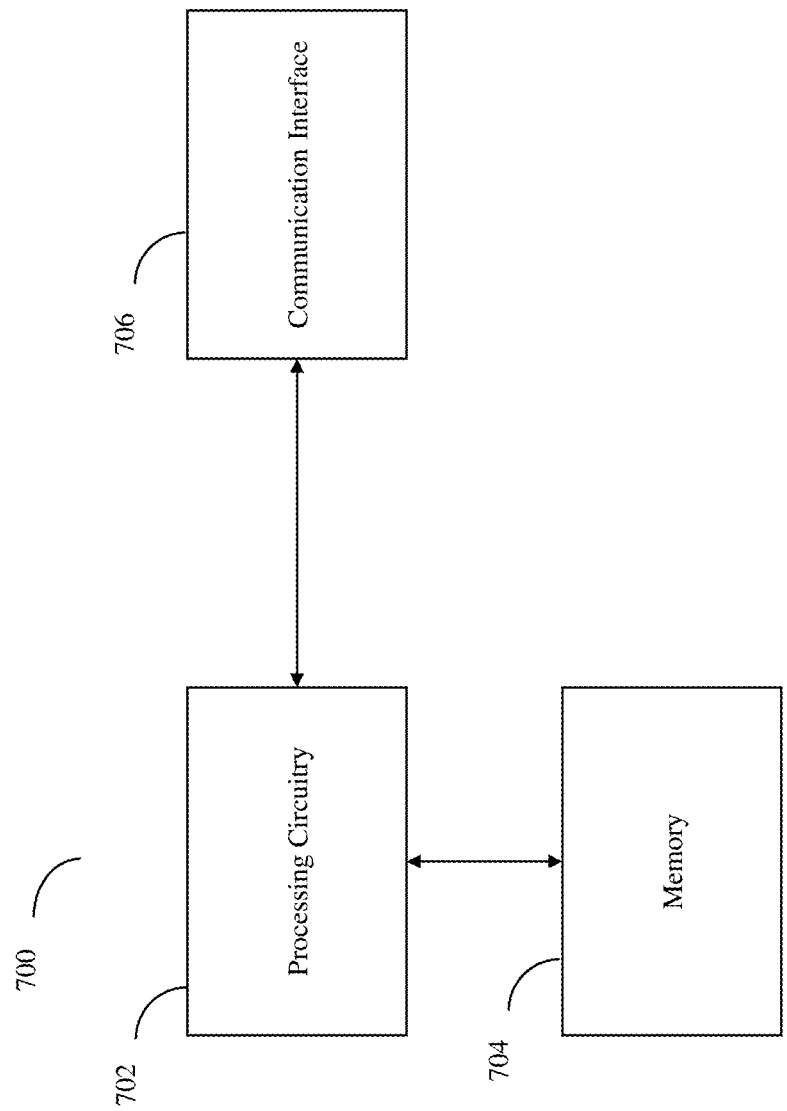
FIG. 7 is a block diagram of an apparatus that may be specifically configured in accordance with an example embodiment.

An apparatus 700 is provided in accordance with an example embodiment as shown in FIG. 7. In one embodiment, the apparatus of FIG. 7 may be embodied by a source 602, such as a file writer which, in turn, may be embodied by a server, that is configured to stream a compressed representation of the media data and associated metadata. In an alternative embodiment, the apparatus may be embodied by a client device 604, such as a file reader which may be embodied, for example, by any of the various computing devices described above. In either of these embodiments and as shown in FIG. 7, the apparatus of an example embodiment includes, is associated with or is in communication with a processing circuitry 702, one or more memory devices 704, a communication interface 706, and optionally a user interface.

The processing circuitry 702 may be in communication with the memory device 704 via a bus for passing information among components of the apparatus 700. The memory device may be non-transitory and may include, for example, one or more volatile and/or non-volatile memories. In other words, for example, the memory device may be an electronic storage device (e.g., a computer readable storage medium) comprising gates configured to store data (e.g., bits) that may be retrievable by a machine (e.g., a computing device like the processing circuitry). The memory device may be configured to store information, data, content, applications, instructions, or the like for enabling the apparatus to carry out various functions in accordance with an example embodiment of the present disclosure. For example, the memory device could be configured to buffer input data for processing by the processing circuitry. Additionally or alternatively, the memory device could be configured to store instructions for execution by the processing circuitry.

The apparatus 700 may, in some embodiments, be embodied in various computing devices as described above. However, in some embodiments, the apparatus may be embodied as a chip or chip set. In other words, the apparatus may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus may therefore, in some cases, be configured to implement an embodiment of the present disclosure on a single chip or as a single 'system on a chip.' As such, in some cases, a chip or chipset may constitute means for performing one or more operations for providing the functionalities described herein.

The processing circuitry 702 may be embodied in a number of different ways. For example, the processing circuitry may be embodied as one or more of various hardware processing means such as a coprocessor, a microprocessor, a controller, a digital signal processor (DSP), a processing element with or without an accompanying DSP, or various other circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processing circuitry may include one or more processing cores configured to perform independently. A multi-core processing circuitry may enable multiprocessing within a single physical package. Additionally or alternatively, the processing circuitry may include one or more processors configured in tandem via the bus to enable independent execution of instructions, pipelining and/or multithreading.

In an example embodiment, the processing circuitry 702 may be configured to execute instructions stored in the memory device 704 or otherwise accessible to the processing circuitry. Alternatively or additionally, the processing circuitry may be configured to execute hard coded functionality. As such, whether configured by hardware or software methods, or by a combination thereof, the processing circuitry may represent an entity (e.g., physically embodied in circuitry) capable of performing operations according to an embodiment of the present disclosure while configured accordingly. Thus, for example, when the processing circuitry is embodied as an ASIC, FPGA or the like, the processing circuitry may be specifically configured hardware for conducting the operations described herein. Alternatively, as another example, when the processing circuitry is embodied as an executor of instructions, the instructions may specifically configure the processing circuitry to perform the algorithms and/or operations described herein when the instructions are executed. However, in some cases, the processing circuitry may be a processor of a specific device (e.g., an image or video processing system) configured to employ an embodiment of the present invention by further configuration of the processing circuitry by instructions for performing the algorithms and/or operations described herein. The processing circuitry may include, among other things, a clock, an arithmetic logic unit (ALU) and logic gates configured to support operation of the processing circuitry.

The communication interface 706 may be any means such as a device or circuitry embodied in either hardware or a combination of hardware and software that is configured to receive and/or transmit data, including video bitstreams. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication. As such, for example, the communication interface may include a communication modem and/or other hardware/software for supporting communication via cable, digital subscriber line (DSL), universal serial bus (USB) or other mechanisms.

In some embodiments, the apparatus 700 may optionally include a user interface that may, in turn, be in communication with the processing circuitry 702 to provide output to a user, such as by outputting an encoded video bitstream and, in some embodiments, to receive an indication of a user input. As such, the user interface may include a display and, in some embodiments, may also include a keyboard, a mouse, a joystick, a touch screen, touch areas, soft keys, a microphone, a speaker, or other input/output mechanisms. Alternatively or additionally, the processing circuitry may comprise user interface circuitry configured to control at least some functions of one or more user interface elements such as a display and, in some embodiments, a speaker, ringer, microphone and/or the like. The processing circuitry and/or user interface circuitry comprising the processing circuitry may be configured to control one or more functions of one or more user interface elements through computer program instructions (e.g., software and/or firmware) stored on a memory accessible to the processing circuitry (e.g., memory device, and/or the like).

Fundamentals of Neural Networks

A neural network (NN) is a computation graph consisting of several layers of computation. Each layer consists of one or more units, where each unit performs a computation. A unit is connected to one or more other units, and a connection may be associated with a weight. The weight may be used for scaling the signal passing through an associated connection. Weights are learnable parameters, for example, values which can be learned from training data. There may be other learnable parameters, such as those of batch-normalization layers.

Couple of examples of architectures for neural networks are feed-forward and recurrent architectures. Feed-forward neural networks are such that there is no feedback loop, each layer takes input from one or more of the previous layers and provides its output as the input for one or more of the subsequent layers. Also, units inside a certain layer take input from units in one or more of preceding layers and provide output to one or more of following layers.

Initial layers, those close to the input data, extract semantically low-level features, for example, edges and textures in images, and intermediate and final layers extract more high-level features. After the feature extraction layers, there may be one or more layers performing a certain task, for example, classification, semantic segmentation, object detection, denoising, style transfer, super-resolution, and the like. In recurrent neural networks, there is a feedback loop, so that the neural network becomes stateful, for example, it is able to memorize information or a state.

Neural networks are being utilized in an ever-increasing number of applications for many different types of devices, for example, mobile phones, chat bots, IoT devices, smart cars, voice assistants, and the like. Some of these applications include, but are not limited to, image and video analysis and processing, social media data analysis, device usage data analysis, and the like.

One of the properties of neural networks, and other machine learning tools, is that they are able to learn properties from input data, either in a supervised way or in an unsupervised way. Such learning is a result of a training algorithm, or of a meta-level neural network providing the training signal.

In general, the training algorithm consists of changing some properties of the neural network so that its output is as close as possible to a desired output. For example, in the case of classification of objects in images, the output of the neural network can be used to derive a class or category index which indicates the class or category that the object in the input image belongs to. Training usually happens by minimizing or decreasing the output error, also referred to as the loss. Examples of losses are mean squared error, cross-entropy, and the like. In recent deep learning techniques, training is an iterative process, where at each iteration the algorithm modifies the weights of the neural network to make a gradual improvement in the network's output, for example, gradually decrease the loss.

Training a neural network is an optimization process, but the final goal is different from the typical goal of optimization. In optimization, the only goal is to minimize a function. In machine learning, the goal of the optimization or training process is to make the model learn the properties of the data distribution from a limited training dataset. In other words, the goal is to learn to use a limited training dataset in order to learn to generalize to previously unseen data, for example, data which was not used for training the model. This is usually referred to as generalization. In practice, data is usually split into at least two sets, the training set and the validation set. The training set is used for training the network, for example, to modify its learnable parameters in order to minimize the loss. The validation set is used for checking the performance of the network on data, which was not used to minimize the loss, as an indication of the final performance of the model. In particular, the errors on the training set and on the validation set are monitored during the training process to understand the following:

when the network is learning at all—in this case, the training set error should decrease, otherwise the model is in the regime of underfitting.

when the network is learning to generalize—in this case, also the validation set error needs to decrease and be not too much higher than the training set error. For example, the validation set error should be less than 20% higher than the training set error. If the training set error is low, for example, 10% of its value at the beginning of training, or with respect to a threshold that may have been determined based on an evaluation metric, but the validation set error is much higher than the training set error, or it does not decrease, or it even increases, the model is in the regime of overfitting. This means that the model has just memorized properties of the training and performs well only on that set, but performs poorly on a set not used for training or tuning its parameters.

Lately, neural networks have been used for compressing and de-compressing data such as images. The most widely used architecture for such task is the auto-encoder, which is a neural network consisting of two parts: a neural encoder and a neural decoder. In various embodiments, these neural encoder and neural decoder would be referred to as encoder and decoder, even though these refer to algorithms which are learned from data instead of being tuned manually. The encoder takes an image as an input and produces a code, to represent the input image, which requires less bits than the input image. This code may have been obtained by a binarization or quantization process after the encoder. The decoder takes in this code and reconstructs the image which was input to the encoder.

Such encoder and decoder are usually trained to minimize a combination of bitrate and distortion, where the distortion is usually mean squared error (MSE), peak signal to noise ratio (PSNR), structural similarity (SSIM) index, or similar metrics. These distortion metrics are meant to be inversely proportional to the human visual perception quality.

In various embodiments, terms 'model', 'neural network', 'neural net' and 'network' may be used interchangeably, and also the weights of neural networks may be sometimes referred to as learnable parameters or as parameters.

Fundamentals of Video/Image Coding

Video codec consists of an encoder that transforms the input video into a compressed representation suited for storage/transmission and a decoder that can decompress the compressed video representation back into a viewable form. Typically, an encoder discards some information in the original video sequence in order to represent the video in a more compact form, for example, at lower bitrate.

Typical hybrid video codecs, for example ITU-T H.263 and H.264, encode the video information in two phases. Firstly, pixel values in a certain picture area (or 'block') are predicted. In an example, the pixel values may be predicted by using motion compensation algorithm. This prediction technique includes finding and indicating an area in one of the previously coded video frames that corresponds closely to the block being coded.

In other example, the pixel values may be predicted by using spatial prediction techniques. This prediction technique uses the pixel values around the block to be coded in a specified manner Secondly, the prediction error, for example, the difference between the predicted block of pixels and the original block of pixels is coded. This is typically done by transforming the difference in pixel values using a specified transform, for example, discrete cosine transform (DCT) or a variant of it; quantizing the coefficients; and entropy coding the quantized coefficients. By varying the fidelity of the quantization process, encoder can control the balance between the accuracy of the pixel representation, for example, picture quality and size of the resulting coded video representation, for example, file size or transmission bitrate.

Inter prediction, which may also be referred to as temporal prediction, motion compensation, or motion-compensated prediction, exploits temporal redundancy. In inter prediction the sources of prediction are previously decoded pictures.

Intra prediction utilizes the fact that adjacent pixels within the same picture are likely to be correlated. Intra prediction can be performed in spatial or transform domain, for example, either sample values or transform coefficients can be predicted. Intra prediction is typically exploited in intra coding, where no inter prediction is applied.

One outcome of the coding procedure is a set of coding parameters, such as motion vectors and quantized transform coefficients. Many parameters can be entropy-coded more efficiently when they are predicted first from spatially or temporally neighboring parameters. For example, a motion vector may be predicted from spatially adjacent motion vectors and only the difference relative to the motion vector predictor may be coded. Prediction of coding parameters and intra prediction may be collectively referred to as in-picture prediction.

The decoder reconstructs the output video by applying prediction techniques similar to the encoder to form a predicted representation of the pixel blocks. For example, using the motion or spatial information created by the encoder and stored in the compressed representation and prediction error decoding, which is inverse operation of the prediction error coding recovering the quantized prediction error signal in spatial pixel domain. After applying prediction and prediction error decoding techniques the decoder sums up the prediction and prediction error signals, for example, pixel values to form the output video frame. The decoder and encoder can also apply additional filtering techniques to improve the quality of the output video before passing it for display and/or storing it as prediction reference for the forthcoming frames in the video sequence.

In typical video codecs the motion information is indicated with motion vectors associated with each motion compensated image block. Each of these motion vectors represents the displacement of the image block in the picture to be coded in the encoder side or decoded in the decoder side and the prediction source block in one of the previously coded or decoded pictures.

In order to represent motion vectors efficiently, the motion vectors are typically coded differentially with respect to block specific predicted motion vectors. In typical video codecs, the predicted motion vectors are created in a predefined way, for example, calculating the median of the encoded or decoded motion vectors of the adjacent blocks.

Another way to create motion vector predictions is to generate a list of candidate predictions from adjacent blocks and/or co-located blocks in temporal reference pictures and signaling the chosen candidate as the motion vector predictor. In addition to predicting the motion vector values, the reference index of previously coded/decoded picture can be predicted. The reference index is typically predicted from adjacent blocks and/or or co-located blocks in temporal reference picture.

Moreover, typical high efficiency video codecs employ an additional motion information coding/decoding mechanism, often called merging/merge mode, where all the motion field information, which includes motion vector and corresponding reference picture index for each available reference picture list, is predicted and used without any modification/correction. Similarly, predicting the motion field information is carried out using the motion field information of adjacent blocks and/or co-located blocks in temporal reference pictures and the used motion field information is signaled among a list of motion field candidate list filled with motion field information of available adjacent/co-located blocks.

In typical video codecs, the prediction residual after motion compensation is first transformed with a transform kernel, for example, DCT and then coded. The reason for this is that often there still exists some correlation among the residual and transform can in many cases help reduce this correlation and provide more efficient coding.

Typical video encoders utilize Lagrangian cost functions to find optimal coding modes, for example, the desired macroblock mode and associated motion vectors. This kind of cost function uses a weighting factor $\lambda$ to tie together the exact or estimated image distortion due to lossy coding methods and the exact or estimated amount of information that is required to represent the pixel values in an image area:

$$C = D + \lambda R \qquad \text{equation 1}$$

In equation 1, C is the Lagrangian cost to be minimized, D is the image distortion, for example, mean squared error with the mode and motion vectors considered, and R is the number of bits needed to represent the required data to reconstruct the image block in the decoder including the amount of data to represent the candidate motion vectors.

An elementary unit for the output of a video encoder and the input of a video decoder, respectively, may be a Network Abstraction Layer (NAL) unit. For transport over packet-oriented networks or storage into structured files, NAL units may be encapsulated into packets or similar structures. A bytestream format encapsulating NAL units may be used for transmission or storage environments that do not provide framing structures. The bytestream format may separate NAL units from each other by attaching a start code in front of each NAL unit. To avoid false detection of NAL unit boundaries, encoders may run a byte-oriented start code emulation prevention algorithm, which may add an emulation prevention byte to the NAL unit payload if a start code would have occurred otherwise. In order to enable straight-forward gateway operation between packet- and stream-oriented systems, start code emulation prevention may be performed regardless of whether the bytestream format is in use or not. A NAL unit may be defined as a syntax structure containing an indication of the type of data to follow and bytes containing that data in the form of a raw byte sequence payload interspersed as necessary with emulation prevention bytes. A raw byte sequence payload (RBSP) may be defined as a syntax structure containing an integer number of bytes that is encapsulated in a NAL unit. An RBSP is either empty or has the form of a string of data bits containing syntax elements followed by an RBSP stop bit and followed by zero or more subsequent bits equal to 0.

In some coding standards, NAL units consist of a header and payload. The NAL unit header indicates the type of the NAL unit. In some coding standards, the NAL unit header indicates a scalability layer identifier (e.g. called nuh_layer_id in H.265/HEVC and H.266/NVC), which could be used e.g. for indicating spatial or quality layers, views of a multiview video, or auxiliary layers (such as depth maps or alpha planes). In some coding standards, the NAL unit header includes a temporal sublayer identifier, which may be used for indicating temporal subsets of the bitstream, such as a 30-frames-per-second subset of a 60-frames-per-second bitstream.

NAL units may be categorized into Video Coding Layer (VCL) NAL units and non-VCL NAL units. VCL NAL units are typically coded slice NAL units.

A non-VCL NAL unit may be, for example, one of the following types: a video parameter set (VPS), a sequence parameter set (SPS), a picture parameter set (PPS), an adaptation parameter set (APS), a supplemental enhancement information (SEI) NAL unit, an access unit delimiter, an end of sequence NAL unit, an end of bitstream NAL unit, or a filler data NAL unit. Parameter sets may be needed for the reconstruction of decoded pictures, whereas many of the other non-VCL NAL units are not necessary for the reconstruction of decoded sample values.

Some coding formats specify parameter sets that may carry parameter values needed for the decoding or reconstruction of decoded pictures. A parameter may be defined as a syntax element of a parameter set. A parameter set may be defined as a syntax structure that contains parameters and that can be referred to from or activated by another syntax structure, for example, using an identifier.

Some types of parameter sets are briefly described in the following, but it needs to be understood, that other types of parameter sets may exist and that embodiments may be applied but are not limited to the described types of parameter sets.

Parameters that remain unchanged through a coded video sequence may be included in a sequence parameter set. Alternatively, the SPS may be limited to apply to a layer that references the SPS, e.g. the SPS may remain valid for a coded layer video sequence. In addition to the parameters that may be needed by the decoding process, the sequence parameter set may optionally contain video usability information (VUI), which includes parameters that may be important for buffering, picture output timing, rendering, and resource reservation.

A picture parameter set contains such parameters that are likely to be unchanged in several coded pictures. A picture parameter set may include parameters that can be referred to by the VCL NAL units of one or more coded pictures.

A video parameter set (VPS) may be defined as a syntax structure containing syntax elements that apply to zero or more entire coded video sequences and may contain parameters applying to multiple layers. VPS may provide information about the dependency relationships of the layers in a bitstream, as well as many other information that are applicable to all slices across all layers in the entire coded video sequence.

A video parameter set RBSP may include parameters that can be referred to by one or more sequence parameter set RBSPs.

The relationship and hierarchy between the VPS, the SPS, and the PPS may be described as follows. A VPS resides one level above an SPS in the parameter set hierarchy and in the context of scalability. The VPS may include parameters that are common for all slices across all layers in the entire coded video sequence. The SPS includes the parameters that are common for all slices in a particular layer in the entire coded video sequence and may be shared by multiple layers. The PPS includes the parameters that are common for all slices in a particular picture and are likely to be shared by all slices in multiple pictures.

The APS may be specified in some coding formats, such as H.266/VVC. The APS may be allowed to apply to one or more image segments, such as slices. In H.266/VVC, the APS may be defined as a syntax structure containing syntax elements that apply to zero or more slices as determined by zero or more syntax elements found in slice headers or in a picture header. The APS may comprise a type (aps_params_type in H.266/VVC) and an identifier (aps_adaptation_parameter_set_id in H.266/VVC). The combination of an APS type and an APS identifier may be used to identify a particular APS. H.266/VVC comprises three APS types: an adaptive loop filtering (ALF), a luma mapping with chroma scaling (LMCS), and a scaling list APS types. The ALF APS(s) are referenced from a slice header (thus, the referenced ALF APSs can change slice by slice), and the LMCS and scaling list APS(s) are referenced from a picture header (thus, the referenced LMCS and scaling list APSs can change picture by picture). In H.266/VVC, the APS RBSP has the following syntax:

|  | Descriptor |
|---|---|
| adaptation_parameter_set_rbsp( ) { |  |
|   aps_params_type | u(3) |
|   aps_adaptation_parameter_set_id | u(5) |
|   aps_chroma_present_flag | u(1) |
|   if( aps_params_type = = ALF_APS ) |  |
|     alf_data( ) |  |
|   else if( aps_params_type = = LMCS_APS ) |  |
|     lmcs_data( ) |  |
|   else if( aps_params_type = = SCALING_APS ) |  |
|     scaling_list_data( ) |  |
|   aps_extension_flag | u(1) |
|   if( aps_extension_flag ) |  |
|     while( more_rbsp_data( ) ) |  |
|       aps_extension_data_flag | u(1) |
|   rbsp_trailing_bits( ) |  |
| } |  |

Many instances of parameter sets may be allowed in a bitstream, and each instance is identified with a unique identifier. In order to limit the memory usage needed for parameter sets, the value range for parameter set identifiers has been limited. Each slice header (in HEVC) or each picture header (in VVC) includes the identifier of the picture parameter set that is active for the decoding of the picture that contains the slice or the picture, respectively, and each picture parameter set contains the identifier of the active sequence parameter set. Consequently, the transmission of picture and sequence parameter sets does not have to be accurately synchronized with the transmission of slices. Instead, it is sufficient that the active sequence and picture parameter sets are received at any moment before they are referenced, which allows transmission of parameter sets 'out-of-band' using a more reliable transmission mechanism compared to the protocols used for the slice data. For example, parameter sets can be included as a parameter in the session description for Real-time Transport Protocol (RTP) sessions. When parameter sets are transmitted in-band, they can be repeated to improve error robustness.

Out-of-band transmission, signaling or storage can additionally or alternatively be used for other purposes than tolerance against transmission errors, such as ease of access or session negotiation. For example, a sample entry of a track in a file conforming to the ISO Base Media File Format may comprise parameter sets, while the coded data in the bitstream is stored elsewhere in the file or in another file.

A parameter set may be activated or referenced by a reference (to its identifier) from a slice, a picture header, or from another active or referenced parameter set or in some cases from another syntax structure.

Video coding specifications may enable the use of supplemental enhancement information (SEI) messages or alike. Some video coding specifications include SEI NAL units, and some video coding specifications contain both prefix SEI NAL units and suffix SEI NAL units. A prefix SEI NAL unit can start a picture unit or alike; and a suffix SEI NAL unit can end a picture unit or alike. Hereafter, an SEI NAL unit may equivalently refer to a prefix SEI NAL unit or a suffix SEI NAL unit. An SEI NAL unit includes one or more SEI messages, which are not required for the decoding of output pictures but may assist in related processes, such as picture output timing, post-processing of decoded pictures, rendering, error detection, error concealment, and resource reservation.

The syntax of an SEI NAL unit may be specified as follows:

| | Descriptor |
|---|---|
| sei_rbsp( ) { <br> do <br> sei_message( ) <br> while( more_rbsp_data( )) <br> rbsp_trailing_bits( ) <br> } | |

The syntax of an SEI message may be specified as follows:

| | Descriptor |
|---|---|
| sei_message( ) { <br> payloadType = 0 <br> do { <br>   payload_type_byte <br>   payloadType += payload_type_byte <br> } while( payload_type_byte = = 0xFF ) <br> payloadSize = 0 <br> do { <br>   payload_size_byte <br>   payloadSize += payload_size_byte <br> } while( payload_size_byte = = 0xFF ) <br> sei_payload( payloadType, payloadSize ) <br> } | <br><br><br><br>u(8)<br><br><br><br><br>u(8) |

The variable payloadType may indicate the type of the SEI message and the variable payloadSize may indicate the number of bytes in the SEI message payload, e.g. sei_payload( ). The syntax and semantics of sei_payload( ) may depend on payloadType.

Several SEI messages are specified in H.264/AVC, H.265/HEVC, H.266/VVC, and H.274/VSEI standards, and the user data SEI messages enable organizations and companies to specify SEI messages for specific use. The standards may contain the syntax and semantics for the specified SEI messages but a process for handling the messages in the recipient might not be defined. Consequently, encoders may be required to follow the standard specifying a SEI message when they create SEI message(s), and decoders might not be required to process SEI messages for output order conformance One of the reasons to include the syntax and semantics of SEI messages in standards is to allow different system specifications to interpret the supplemental information identically and hence interoperate. It is intended that system specifications can require the use of particular SEI messages both in the encoding end and in the decoding end, and additionally the process for handling particular SEI messages in the recipient can be specified.

A design principle has been followed for SEI message specifications: the SEI messages are generally not extended in future amendments or versions of the standard.

An SEI prefix indication SEI message has been specified in the H.265/HEVC standard. The SEI prefix indication SEI message carries one or more SEI prefix indications for SEI messages of a particular value of SEI payload type (payloadType). Each SEI prefix indication is a bit string that follows the SEI payload syntax of that value of payloadType and contains a number of complete syntax elements starting from the first syntax element in the SEI payload.

Each SEI prefix indication for an SEI message of a particular value of payloadType indicates that one or more SEI messages of this value of payloadType are expected or likely to be present in the coded video sequence (CVS) and to start with the provided bit string. A starting bit string would typically contain only a true subset of an SEI payload of the type of SEI message indicated by the payloadType, may contain a complete SEI payload, and shall not contain more than a complete SEI payload. It is not prohibited for SEI messages of the indicated value of payloadType to be present that do not start with any of the indicated bit strings.

SEI prefix indications should provide sufficient information for indicating what type of processing is needed or what type of content is included. The former (type of processing) indicates decoder-side processing capability, e.g., whether some type of frame unpacking is needed. The latter (type of content) indicates, for example, whether the bitstream contains subtitle captions in a particular language.

The content of an SEI prefix indication SEI message may, for example, be used by transport-layer or systems-layer processing elements to determine whether the CVS is suitable for delivery to a receiving and decoding system, based on whether the receiving system can properly process the CVS to enable an adequate user experience or whether the CVS satisfies the application needs.

The phrase along the bitstream (e.g. indicating along the bitstream) or along a coded unit of a bitstream (e.g. indicating along a coded tile) may be used in claims and described embodiments to refer to transmission, signaling, or storage in a manner that the 'out-of-band' data is associated with, but not included within, the bitstream or the coded unit, respectively. The phrase decoding along the bitstream or along a coded unit of a bitstream or alike may refer to decoding the referred out-of-band data (which may be obtained from out-of-band transmission, signaling, or storage) that is associated with the bitstream or the coded unit, respectively. For example, the phrase along the bitstream may be used when the bitstream is contained in a container file, such as a file conforming to the ISO Base Media File Format, and certain file metadata is stored in the file in a manner that associates the metadata to the bitstream, such as boxes in the sample entry for a track containing the bitstream, a sample group for the track containing the bitstream, or a timed metadata track associated with the track containing the bitstream. In another example, the phrase along the bitstream may be used when the bitstream is made available as a stream over a communication protocol and a media description, such as a streaming manifest, is provided to describe the stream.

A bitstream may be defined to logically include a syntax structure, such as a NAL unit, when the syntax structure is transmitted along the bitstream but could be included in the bitstream according to the bitstream format. A bitstream may be defined to natively comprise a syntax structure, when the bitstream includes the syntax structure.

An independently parsable structure within a container structure may be defined to be such a structure that can be parsed or decoded without fully parsing or decoding earlier structures or syntax elements in the same container structure. For example, SEI messages within an SEI NAL unit are independently parsable, since parsing of any earlier SEI message in the same SEI NAL unit can be skipped by resolving payloadSize and skipping the number of bytes indicated by payloadSize. Another example of an independently parsable structures is a syntax structure at a pre-defined bit position within a container structure. Yet another way to achieve independently parsable structures is to include position offsets to independently parsable structures into a container structure, wherein the bit position of an independently parsable structure is derivable from one or more of the position offsets.

Filters in Video Codecs

Conventional image and video codecs use a set of filters to enhance the visual quality of the predicted visual content and can be applied either in-loop or out-of-loop, or both. In the case of in-loop filters, the filter applied on one block in the currently-encoded frame may affect the encoding of another block in the same frame and/or in another frame which is predicted from the current frame. An in-loop filter can affect the bitrate and/or the visual quality. An enhanced block may cause a smaller residual, difference between original block and predicted-and-filtered block, thus using less bits in the bitstream output by the encoder. An out-of-loop filter may be applied on a frame after it has been reconstructed, the filtered visual content may not be a source for prediction, and thus it may only impact the visual quality of the frames that are output by the decoder.

Video Coding for Machines (VCM)

Reducing the distortion in image and video compression is often intended to increase human perceptual quality, as humans are considered to be the end users, e.g. consuming or watching the decoded images or videos. Recently, with the advent of machine learning, especially deep learning, there is a rising number of machines (e.g., autonomous agents) that analyze data independently from humans and may even take decisions based on the analysis results without human intervention. Examples of such analysis are object detection, scene classification, semantic segmentation, video event detection, anomaly detection, pedestrian tracking, and the like. Example use cases and applications are self-driving cars, video surveillance cameras and public safety, smart sensor networks, smart TV and smart advertisement, person re-identification, smart traffic monitoring, drones, and the like. Accordingly, when decoded data is consumed by machines, a quality metric for the decoded data may be defined, which is different from a quality metric for human perceptual quality, when considering media compression in inter-machine communications. Also, dedicated algorithms for compressing and decompressing data for machine consumption are likely to be different than those for compressing and decompressing data for human consumption. The set of tools and concepts for compressing and decompressing data for machine consumption is referred to here as video coding for machines.

It is likely that the receiver-side device has multiple 'machines' or neural networks (NNs). These multiple machines may be used in a certain combination which is, for example, determined by an orchestrator sub-system. The multiple machines may be used, for example, in temporal succession, based on the output of the previously used machine, and/or in parallel. For example, a video which was compressed and then decompressed may be analyzed by one machine (NN) for detecting pedestrians, by another machine (another NN) for detecting cars, and by another machine (another NN) for estimating the depth of objects in the frames.

In various embodiments, machine and neural network may be referred interchangeably, and may mean to include, any process or algorithm (e.g. learned or not learned from data) which analyzes or processes data for a certain task. Following paragraphs may specify in further details other assumptions made regarding the machines considered in various embodiments of the invention.

Also, term 'receiver-side' or 'decoder-side' refers to a physical or abstract entity or device which contains one or more machines, circuits or algorithms; and runs these one or more machines on some encoded and eventually decoded video representation which is encoded by another physical or abstract entity or device, for example, the 'encoder-side device'.

The encoded video data may be stored into a memory device, for example, as a file. The stored file may later be provided to another device.

Alternatively, the encoded video data may be streamed from one device to another.

Figure 8:
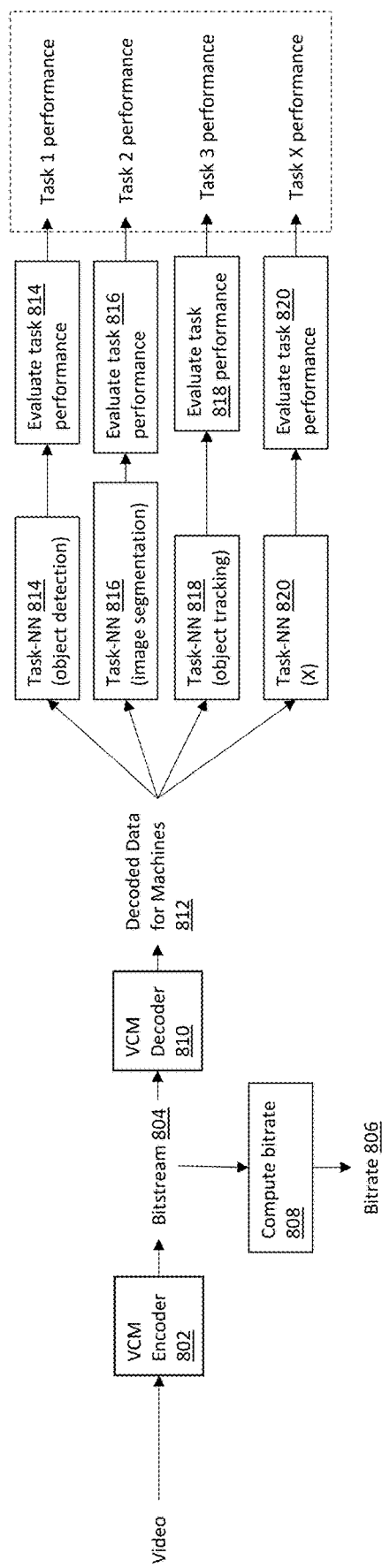
FIG. 8 illustrates a pipeline of video coding for machines (VCM), in accordance of an embodiment.

FIG. 8 illustrates a pipeline of video coding for machines (VCM), in accordance of an embodiment. A VCM encoder 802 encodes the input video into a bitstream 804. A bitrate 806 may be computed 808 from the bitstream 804 in order to evaluate the size of the bitstream 804. A VCM decoder 810 decodes the bitstream 804 output by the VCM encoder 802. An output of the VCM decoder 810 may be referred, for example, as decoded data for machines 812. This data may be considered as the decoded or reconstructed video. However, in some implementations of the pipeline of VCM, the decoded data for machines 812 may not have same or similar characteristics as the original video which was input to the VCM encoder 802. For example, this data may not be easily understandable by a human by simply rendering the data onto a screen. The output of VCM decoder 810 is then input to one or more task neural network (task-NN). For the sake of illustration, FIG. 8 is shown to include three example task-NNs, a task-NN 814 for object detection, a task 816 for image segmentation, a task 818 for object tracking, and a non-specified one, a task-NN 820 for performing task X. The goal of VCM is to obtain a low bitrate while guaranteeing that the task-NNs still perform well in terms of the evaluation metric associated to each task.

Figure 9:
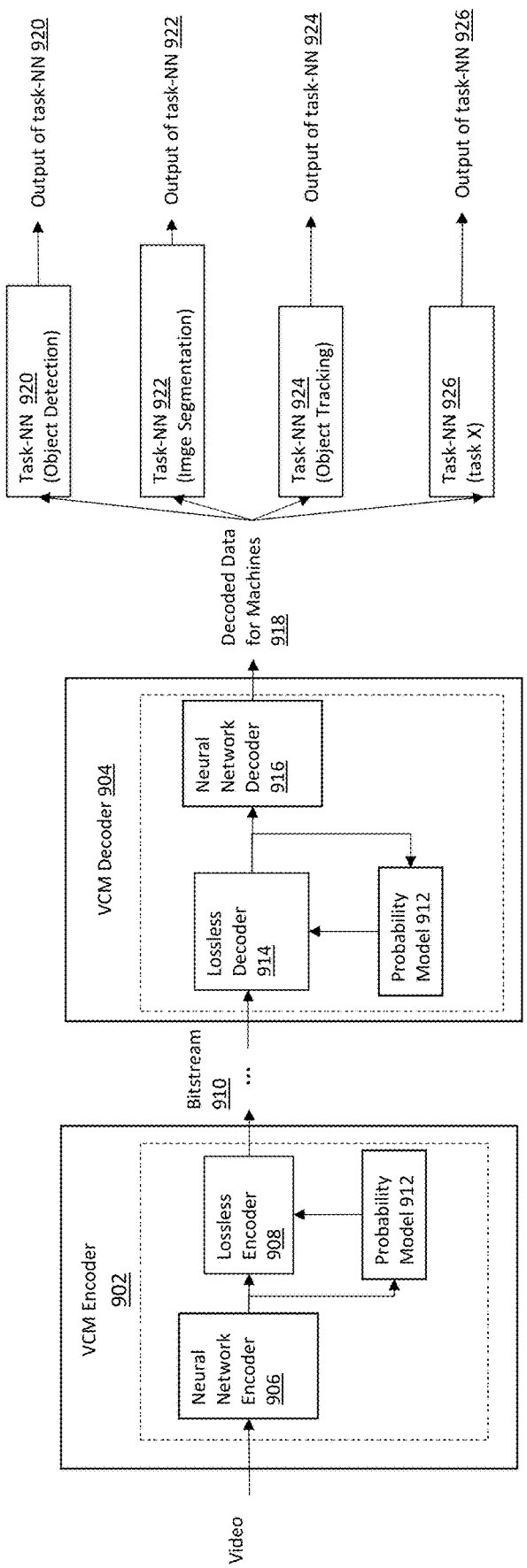
FIG. 9 illustrates an example of an end-to-end learned approach, in accordance with an embodiment.

One of the possible approaches to realize video coding for machines is an end-to-end learned approach. FIG. 9 illustrates an example of an end-to-end learned approach, in accordance with an embodiment. In this approach, the VCM encoder 902 and VCM decoder 904 mainly consist of neural networks. The video is input to a neural network encoder 906. The output of the neural network encoder 906 is input to a lossless encoder 908, such as an arithmetic encoder, which outputs a bitstream 910. The lossless codec may be a probability model 912, both in the lossless encoder 908 and in a lossless decoder 914, which predicts the probability of the next symbol to be encoded and decoded. The probability model 912 may also be learned, for example it may be a neural network. At a decoder-side, the bitstream 910 is input to the lossless decoder 914, such as an arithmetic decoder, whose output is input to a neural network decoder 916. The output of the neural network decoder 916 is the decoded data for machines 918, that may be input to one or more task-NNs, task-NN 920 for object detection, task 922 for image segmentation, task 924 for object tracking, and a non-specified one, task-NN 926 for performing task X.

Figure 10:
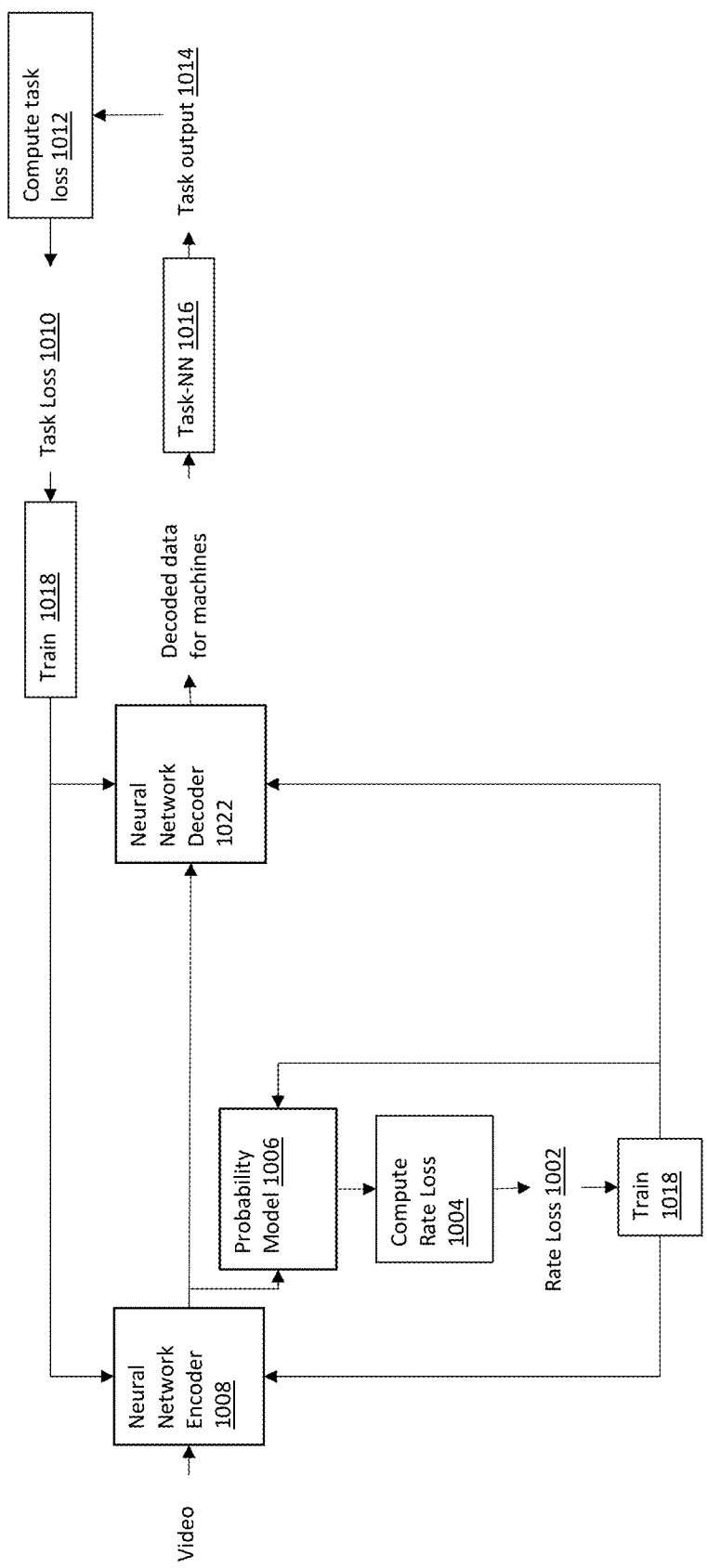
FIG. 10 illustrates an example of how the end-to-end learned system may be trained, in accordance with an embodiment.

FIG. 10 illustrates an example of how the end-to-end learned system may be trained, in accordance with an embodiment. For the sake of simplicity, this embodiment is explained with the help of one task-NN. However, it may be understood that multiple task-NNs may be similarly used in the training process. A rate loss 1002 may be computed 1004 from the output of a probability model 1006. The rate loss 1002 provides an approximation of the bitrate required to encode the input video data, for example, by a neural network encoder 1008. A task loss 1010 may be computed 1012 from a task output 1014 of a task-NN 1016.

The rate loss 1002 and the task loss 1010 may then be used to train 1018 the neural networks used in the system, such as a neural network encoder 1008, a probability model, a neural network decoder 1022. Training may be performed by first computing gradients of each loss with respect to the neural networks that are contributing or affecting the computation of that loss. The gradients are then used by an optimization method, such as Adam, for updating the trainable parameters of the neural networks.

Another possible approach to realize video coding for machines is to use a video codec which is mainly based on more conventional components, that is components which are not obtained or derived by machine learning means. For example, H.266/VVC codec can be used. However, some of the components of such a codec may still be obtained or derived by machine learning means. In one example, one or more of the in-loop filters of the video codec may be a neural network. In another example, a neural network may be used as a post-processing operation (out-of-loop). A neural network filter or other type of filter may be used in-loop or out-of-loop for adapting the reconstructed or decoded frames in order to improve the performance or accuracy of one or more machine neural networks.

In some implementations, machine tasks may be performed at decoder side (instead of at encoder side). Some reasons for performing machine tasks at decoder side include, for example, the encoder-side device may not have the capabilities (computational, power, memory, and the like) for running the neural networks that perform these tasks, or some aspects or the performance of the task neural networks may have changed or improved by the time that the decoder-side device needs the tasks results (e.g., different or additional semantic classes, better neural network architecture). Also, there could be a customization need, where different clients may run different neural networks for performing these machine learning tasks.

Figure 11:
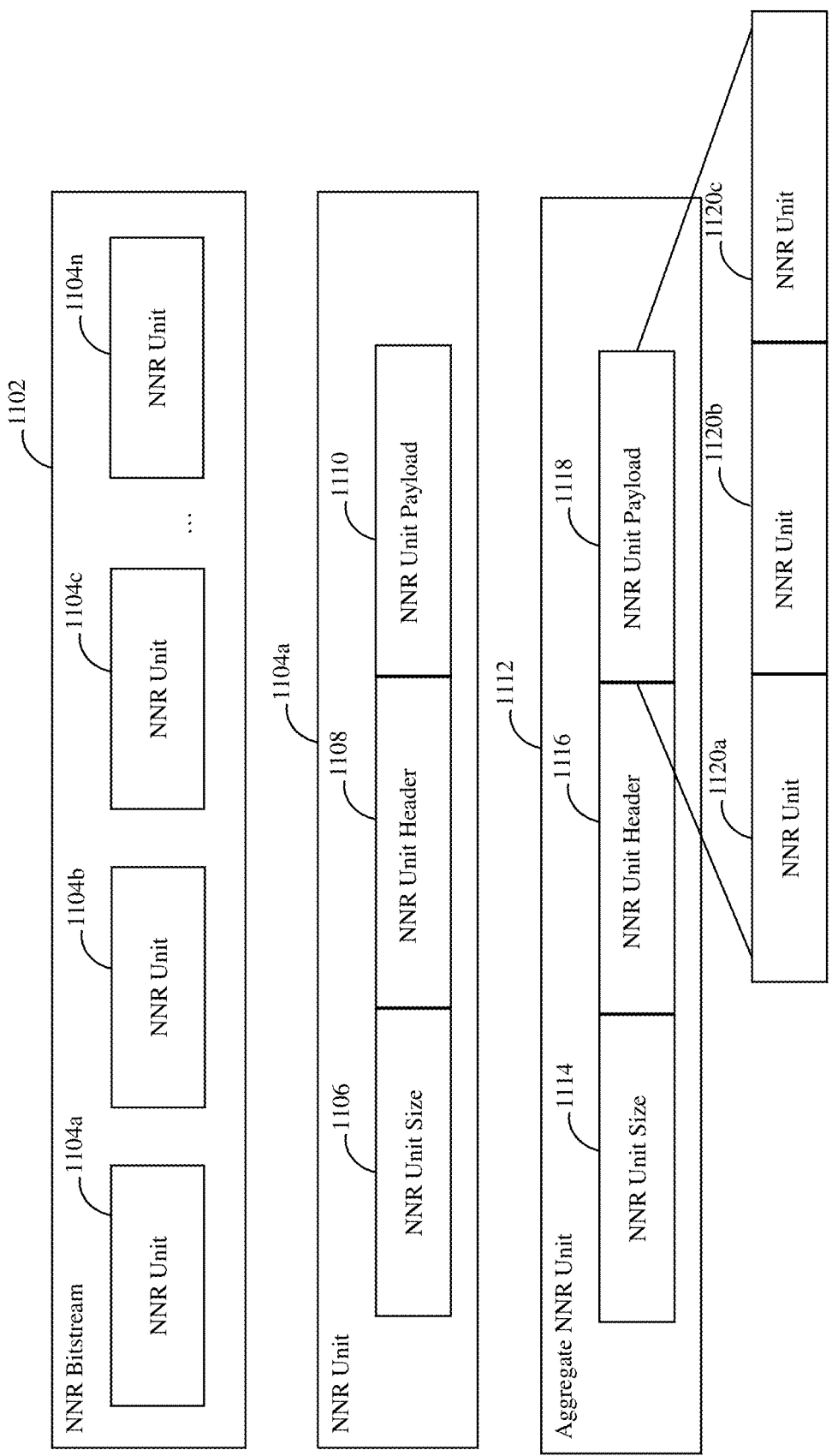
FIG. 11 illustrates an example structure of an NNR bitstream.

FIG. 11 illustrates example structure of a neural network representations (NNR) bitstream. An NNR bitstream may conform to ISO/IEC 15938-17 (compression of neural networks for multimedia content description and analysis). NNR specifies a high-level bitstream syntax (HLS) for signaling compressed neural network data in a channel as a sequence of NNR Units as illustrated in FIG. 11. As depicted in FIG. 11, according to this structure, an NNR bitstream 1102 includes multiple elemental units termed NNR units (e.g. NNR units 1104a, 1104b, 1104c, . . . 1104n). An NNR Unit (e.g. 1104a) represents a basic high-level syntax structure, and includes three syntax elements: an NNR unit Size 1106, an NNR unit header 1108, an NNR unit payload 1110.

In some embodiments, NNR bitstream may include one or more aggregate NNR units. An aggregate NNR unit, for example, an aggregate NNR unit 1112 may include an NNR unit size 1114, an NNR unit header 1116, and an NNR unit payload 1118. An NNR unit payload of aggregate NNR unit may include one or more NNR units. As shown in FIG. 11, the NNR unit payload 1118 includes an NNR unit 1120a, an NNR unit 1120b, and an NNR 1120c. The NNR units 1120a, 1120b, and 1120c may include an NNR unit size, an NNR unit header, and an NNR unit payload, each of which may contain zero or more syntax elements.

As mentioned above, a bitstream may be formed by concatenating several NNR units, aggregate NNR units, or combination thereof. NNR units may contain different types of data. The type of data that is contained in the payload of an NNR unit defines the NNR unit's type. This type is specified in the NNR unit header. The following table specifies the NNR unit header types and their identifiers.

| nnr_unit_type | Identifier | NNR Unit Type | Description |
| --- | --- | --- | --- |
| 0 | NNR_STR | NNR start unit | Compressed neural network bitstream start indicator |
| 1 | NNR_MPS | NNR model parameter set data unit | Neural network global metadata and information |
| 2 | NNR_LPS | NNR layer parameter set data unit | Metadata related to a partial representation of neural network |
| 3 | NNR_TPL | NNR topology data unit | Neural network topology information |
| 4 | NNR_QNT | NNR quantization data unit | Neural network quantization information |
| 5 | NNR_NDU | NNR compressed data unit | Compressed neural network data |

| nnr_unit_type | Identifier | NNR Unit Type | Description |
| --- | --- | --- | --- |
| 6 | NNR_AGG | NNR aggregate unit | NNR unit with payload containing multiple NNR units |
| 7 ... 31 | NNR_RSVD | Reserved | MPEG-reserved range |
| 32 ... 63 | NNR_UNSP | Unspecified | Unspecified range |

An NNR unit is data structure for carrying neural network data and related metadata which is compressed or represented using this specification. NNR units carry compressed or uncompressed information about neural network metadata, topology information, complete or partial layer data, filters, kernels, biases, quantization weights, tensors, or the like. An NNR unit may include following data elements:

NNR unit size: This data element signals the total byte size of the NNR Unit, including the NNR unit size.

NNR unit header: This data element contains information about the NNR unit type and related metadata.

NNR unit payload: This data element contains compressed or uncompressed data related to the neural network.

An NNR bitstream is composed of a sequence of NNR units and/or aggregate NNR units. The first NNR unit in an NNR bitstream shall be an NNR start unit (e.g. NNR unit of type NNR_STR).

Neural Network topology information may be carried as NNR units of type NNR_TPL. Compressed NN information can be carried as NNR units of type NNR_NDU. Parameter sets may be carried as NNR units of type NNR_MPS and NNR_LPS. An NNR bitstream is formed by serializing these units.

Image and video codecs may use one or more neural networks at decoder side, either within the decoding loop or as a post-processing step, for both human-targeted and machine targeted compression.

Following paragraphs describe some non-exhaustive examples of purposes of these decoder-side neural networks:

Enhancing the quality for human consumption. This may comprise concealment of compression artefacts, for example, ringing and blocking.

Spatial upsampling, sometimes referred to as super-resolution.

Temporal upsampling, or frame-rate upsampling. For example, by interpolating between different frames.

Concealment of transmission errors.

Application of specific perceptual 'effect', for example, bokeh, sharpening, and the like.

Enhancing the accuracy of machine analysis tasks, for example, computer vision tasks. This purpose may be broken into multiple purposes, based on the specific computer vision task, for example:

Enhancing for object detection;
Enhancing for object classification;
Enhancing for image/scene/context classification;
Enhancing for video action or activity classification; and
Enhancing for image or video segmentation.

In the case of video, the neural network operation may be applied separately to each of the frames, separately to some of the frames, jointly to a set of frames, to one or more regions of one or more frame, and the like.

However, there is no standardized way to signal to the decoder side which neural network topology and set of weights to use for a certain encoded image or frame or set of frames.

A mechanism is needed to signal a purpose for neural network (NN) operation in an extensible way and associate a general-purpose NN representation with the indicated purpose.

Various embodiments propose mechanisms for signaling the purpose of one or more neural networks that are associated to one or more image or frames, where the neural networks are to be applied at decoder side. Signaling the purpose of one or more neural networks has multiple benefits, including but not limited to being able to select which neural network among multiple available ones is applicable for the need(s) or task(s) of the client or alike.

In an example embodiment, a solution based on high-level syntax for an SEI message is proposed. The SEI message includes information about the purpose, and the MPEG-NNR bitstream representing the neural network or an update of the neural network.

In another example embodiment, the SEI message may comprise multiple purposes, where the neural networks associated to these purposes share layers.

In yet another embodiment, the SEI message may comprise a persistence scope.

In still another embodiment, the SEI message may comprise indicating pre-defined filters.

Solution Based on SEI Message

In this embodiment, an SEI message (NN SEI) which includes information about the purpose of one or more neural network that may be applied within or outside of the decoding operation is proposed.

Figure 12:
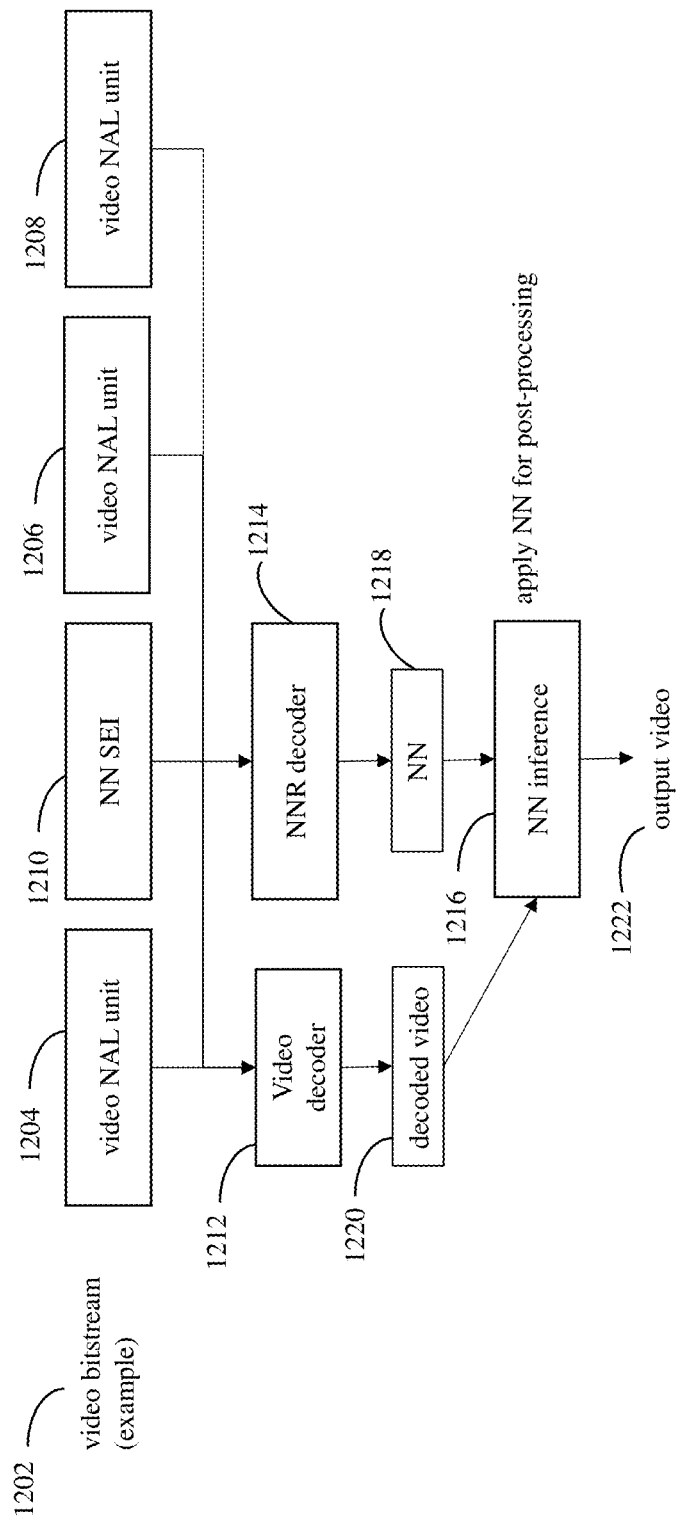
FIG. 12 illustrates an example of operations performed at a decoder side device for enhancing of media frames, in accordance with an embodiment.

FIG. 12 illustrates an example of operations performed at a decoder side device for enhancing of video frames, in accordance with an embodiment. In an embodiment, the enhancing of video frames includes case of post-processing enhancing of video frames. An input video bitstream 1202 may be comprised of video NAL units (for example, video NAL units 1204, 1206, and 1208) and an NN SEI (for example, an NN SEI 1210), where the NN SEI includes SEI message proposed in this embodiment. The video NAL units 1204, 1206, and 1208 are decoded by a video decoder 1212, such as a H.266-compliant decoder. The NN SEI 1210 is first parsed in order to extract the MPEG-NNR bitstream and then a MPEG-NNR-compliant decoder, for example, NNR decoder 1214 is used to decode the NNR bitstream. The decoded neural network (NN) is then used to enhance or filter the decoded video frames which are associated with that NN. For example, an inference module or circuit 1216 may use NN 1218 to enhance or filter decoded frames, from a decoded video 1220, which are associated with NN 1218 to output an output video 1222.

An example version of the NN SEI message may include the following structure:

```
sei_container{
    purpose_sei_message( );
    filter_sei_message( );
}
``` where sei_container may e.g. be a filter nesting SEI message or an SEI NAL unit. The sei_container structure may include SEI messages describing one or more filtering operations and related information.

The SEI message type of purpose_sei_message( ) may be used to identify the purpose of the SEI message content. The payload of the sei_container may be required to contain purpose_sei_message( ) (e.g. as the first SEI message). purpose_sei_message( ) is an SEI message that specifies the purpose for filtering specified within the sei_container( ). The purpose may comprise but is not limited to one or more of purposes listed earlier.

In an embodiment, purpose_sei_message( ) is a logical placeholder for any specific SEI message that defines the purpose. In other words, sei_container( ) comprises such an SEI message in place of purpose_sei_message( ) that specifies the purpose. The payload type value of the SEI message may indicate the purpose and the payload of the SEI message may contain parameters that may further characterize the purpose. According to this embodiment, new purposes may be introduced by defining new SEI messages and multiple purposes for filtering may be indicated by including multiple purpose SEI messages in the same sei_container( ).

In another embodiment, purpose_sei_message is an SEI message whose payload may comprise one or more syntax elements specifying the purpose. In an embodiment, a purpose can be enumerated as a list of known purposes. Such information could be then signalled inside the purpose_sei_message( ).

In yet another embodiment, a purpose may be indicated as an independent syntax element inside the sei_container( ). The syntax element value can be selected among a list of enumerated known purposes.

In an embodiment, when a video decoder (or alike) does not recognize the SEI message type of a contained SEI message, such as the SEI message type of purpose_sei_message( ), it should omit the sei_container( ).

The payload of the sei_container may be required to contain filter_sei_message( ) (e.g. as the second SEI message), which is an SEI message that specifies the filter to be applied. filter_sei_message( ) may for example contain an MPEG-NNR bitstream.

An example of associated syntax for H.266/VVC specification is as follows:

| | Descriptor |
|---|---|
| sei_payload( payloadType, payloadSize ) { | |
|   if( nal_unit_type = = PREFIX_SEI_NUT ) | |
|     ... | |
|     else if( payloadType = = XX1 ) | |
|       postprocessing_filter_nesting( payloadSize ) /* Specified in Rec. ITU-T H.274 \| ISO/IEC 23002-7 */ | |
|     else if( payloadType = = XX2 ) | |
|       resampling_filter_info( payloadSize ) /* Specified in Rec. ITU-T H.274 \| ISO/IEC 23002-7 */ | |
|     else if( payloadType = = XX3 ) | |
|       nnr_filter( payloadSize ) /* Specified in ISO/IEC 15938-17 */ | |
|   ... | |
|   else /* nal_unit_type = = SUFFIX_SEI_NUT */ | |
|     ... | |
|     else if( payloadType = = XX1 ) | |
|       postprocessing_filter_nesting( payloadSize ) /* Specified in Rec. ITU-T H.274 \| ISO/IEC 23002-7 */ | |
|     ... | |
|   } | |
| } | |

XX1, XX2, and XX3 are constant values, which are intended to be selected during the standardization process. In an embodiment, XX1, XX2 and XX3 values are manually selected. In another embodiment, XX1, XX2 and XX3 values are selected automatically.

postprocessing_filter_nesting( ) is an example of the sei_container structure.

resampling_filter_info( ) is an example of one purpose_sei_message structure, which specifies the purpose to be resampling of output picture(s).

nnr_filter( ) is an example of one filter_sei_message( ), which specifies a neural network as an MPEG-NNR coded bitstream, where the neural network is used as a filter for output picture(s).

In another embodiment, NN data may be stored as a serialized binary data which is compliant with an NN processing framework or exchange format such as, but not limited to, NNEF, ONNX, PyTorch or Tensorflow. filter_sei_message( ) may comprise serialized binary neural network data.

An example of associated syntax for H.274/VSEI specification is as follows:

| | Descriptor |
|---|---|
| postprocessing_filter_nesting( payloadSize ) { | |
|   ppfn_num_seis_minus2 | ue(v) |
|   while( !byte_aligned( ) ) | |
|     ppfn_zero_bit /* equal to 0 */ | u(1) |
|   for( i = 0; i <= ppfn_num_seis_minus2 + 1; i++ ) | |
|     sei_message( ) | |
| } | |

| | Descriptor |
|---|---|
| resampling_filter_info( payloadSize ) { | |
|   min_scaling_ratio_hor | u(16) |
|   min_scaling_ratio_ver | u(16) |
|   max_scaling_ratio_hor | u(16) |
|   max_scaling_ratio_ver | u(16) |
| } | | ppfn_num_seis_minus2 plus 2 specifies the number of the SEI messages (sei_message( )) nested in this post-processing filter nesting SEI message.

min_scaling_ratio_hor and min_scaling_ratio_ver specifies the minimum horizontal and vertical scaling ratio, respectively, for which this filter is suggested to be applied in 8.8 fixed point representation.

max_scaling_ratio_hor and max_scaling_ratio_ver specify the maximum horizontal and vertical scaling ratio, respectively, for which this filter is suggested to be applied in, for example, 8.8 fixed point representation.

The following pseudo-code shows a filter_container structure that specifies:

the purpose of the filtering to be resampling within the scaling ratio from 1 (exclusive) to 4 (inclusive) both horizontally and vertically.

an MPEG-NNR bitstream that specifies the neural network filter to be used for the resampling filtering.

| | Value |
|---|---|
| postprocessing_filter_nesting( payloadSize ) { | |
|   ppfn_num_seis_minus2 | 0 |
|   while( !byte_aligned( ) ) | |
|     ppfn_zero_bit /* equal to 0 */ | 0 |
|   // for( i = 0; i <= ppfn_num_seis_minus2 + 1; i++ ) { | |
|     // i equal to 0 | |
|     resampling_filter_info { | |
|       min_scaling_ratio_hor | 257 |
|       min_scaling_ratio_ver | 257 |
|       max_scaling_ratio_hor | 1024 |
|       max_scaling_ratio_ver | 1024 |
|     } | |
|     // i equal to 1 | |
|     nnr_filter( ) | |
| } | |

In an embodiment, associated gain is signaled using the following conceptual syntax or alike:

```
sei_container{
    purpose_sei_message( );
    filter_sei_message( );
    gain_sei_message( );
}
```

The payload of the sei_container may be required to contain also gain_sei_message( ) (e.g. as the third SEI message), which is an SEI message that specifies the expected gain that can be achieved when the neural network signalled in filter_sei_message( ) is applied, where the gain is expressed with respect to one or more predefined metrics that are associated to the purpose specified in the purpose_sei_message( ).

For example, when the purpose is enhancement for scene classification, the gain may be expressed as expected percentage points in classification accuracy.

In another example, when the purpose is visual quality enhancement, the gain may be expressed as expected PSNR improvement, or MS-SSIM improvement.

This way, the decoder side application may decide whether or not to apply the NN based on the expected gain and other factors such as computational complexity of the neural network, available resources of the decoder side devices, and the like.

In an embodiment, instead of signaling the expected gain in gain_sei_message( ), the gain according to any example above may be contained in one or more syntax elements within a purpose_sei_message( ).

Example Embodiments Describing Multiple Purposes, with Shared Layers

In an embodiment, the following conceptual syntax or alike is used:

```
sei_container{
    purpose_sei_message( );
    purpose_specific_topology_sei_message( );
    filter_sei_message( );
}
``` purpose_sei_message( ) may also specify more than one purpose. In this embodiment, a purpose_specific_topology_sei_message( ) is present in the payload of sei_container( ) (e.g. as the second SEI message) and specifies the subsets of topology of the NN present in filter_sei_message( ) that perform the purposes specified in purpose_sei_message( ).

For example, if there are two purposes, such as segmentation and quality enhancement, purpose_specific_topology_sei_message( ) may specify two subsets of the NN topology, where one subset is a list of layers for performing segmentation, and another subset is a list of layers for performing quality enhancement. The two subsets may share some of the NN layers.

In an embodiment, a purpose_specific_topology_sei_message( ) specifies a subset of the NN topology that applies to a single purpose. The order of the SEI messages within the sei_container( ) may determine the purpose that is associated with the purpose_specific_topology_sei_message( ). For example, the purpose_sei_message( ) that immediately precedes the purpose_specific_topology_sei_message( ) may contain the purpose to which the subset of the NN topology applies.

In an embodiment, a subset of the NN topology, if any, is specified by zero or more syntax elements in purpose_sei_message( ).

In an embodiment, a common subset of topology for all indicated purposes is signaled e.g. in common_topology_sei_message( ) contained in the sei_container( ). The common subset of the topology may, for example, be indicated as a list of layers. In addition, purpose-specific subsets of topology may be signaled for none, some, or all indicated purposes.

In an embodiment, when more than one purpose is indicated in the sei_container( ) (e.g., by having multiple instances of purpose_sei_message( ) or by including multiple purposes in a single purpose_sei_message( )), the filter_sei_message( ) may contain a neural network representation which has a common subset of layers and purpose-specific subsets of layers. For example, the first few layers are the common subset, and the following layers represent purpose-specific subset of layers, arranged as parallel branches which branch-out from the last layer in the common subset of layers. A neural network which may be used for both segmentation and quality enhancement may, for example, have an initial common subset of layers, followed by two branches. The output of two branches represents the segmentation and the quality enhancement results.

Example Embodiments Indicating a Persistence Scope

In an embodiment, the following conceptual syntax or alike is used:

```
sei_container{
    purpose_sei_message( );
    filter_sei_message( );
    scope_sei_message( );
}
```

The payload of the sei_container may be required to contain an SEI message (e.g. as the third SEI message) that specifies the scope within which the filter is valid. The scope may be expressed, for example, as:
- a picture order count (POC) range relative to the POC value of the picture unit containing the SEI message;
- a temporal duration;
- a number of frames; or
- a spatial scope, which indicates the areas within one or more frames for which the filter is valid. In this case, the temporal scope is assumed to be known at the decoder side. The spatial scope may be a list or set of spatial coordinates with respect to a predefined coordinate system.
- a spatio-temporal scope where both region coordinates within frame(s) and temporal duration (or alike) are specified.

In some embodiments, the temporal or spatio-temporal scope may refer to non-connected portions of the video, for example, a filter may be applied from frame 1 to frame 150 and from frame 400 to frame 470.

Another Example Embodiment Indicating a Persistence Scope

The sei_container( ) contains an identifier for a specific neural network (e.g. ppfn_id). A filter activation SEI message may include a ppfn_id value that is activated for a temporal scope, spatial scope or spatio-temporal scope determined by the filter activation SEI message. The filter with a particular ppfn_id value can be overwritten or updated by a subsequent sei_container( ) containing that ppfn_id value.

Yet Another Example Embodiment Indicating a Persistence Scope

In an example, the scope pertains valid from the position of the sei_container structure until a specific 'event' appears in the bitstream, which may e.g. be one or more of the following:
- the end of a coded video sequence (for a single-layer bitstream) or the end of a coded layer video sequence (for a multi-layer bitstream);
- another sei_container structure appears; or
- another sei_container structure or other signal indicating that the previous sei_container structure is canceled.

When more than one 'event' type may be possible, the sei_container( ) is valid until the next event, regardless of its type. For example, the sei_container( ) may be valid until the end of the coded layer video sequence or a subsequent sei_container( ), whichever is next in the bitstream.

sei_container may include a 'cancel flag' that turns off filtering.

In an embodiment, prerequisites for applying the filtering are signaled using the following conceptual syntax or alike:

```
sei_container{
    purpose_sei_message( );
    filter_sei_message( );
    prerequisite_sei_message( );
}
```

The payload of the sei_container may comprise a prerequisite_sei_message( ), which is an SEI message that specifies the prerequisites for applying the filtering in in filter_sei_message( ). Prerequisites may comprise properties of the playback device (e.g. ambient light intensity, screen brightness, contrast, pixel density or resolution and alike).

For example, when filtering is to be applied only for certain display resolutions, the prerequisite_sei_message( ) may contain the resolution range for which the filtering is valid.

In an embodiment, instead of signaling the prerequisites in prerequisite_sei_message( ), the prerequisites may be included in one or more syntax elements within a purpose_sei_message( ).

In an embodiment, essentiality of one or more prerequisites may be signaled. For example, it may be signaled that a prerequisite must be fulfilled in order to apply the filtering. In another example, it may be signaled that a prerequisite is recommended to be fulfilled in order to apply the filtering.

In an embodiment, a prerequisite_sei_message( ) or any similar structure comprises a complexity requirement, such as, but not limited to, one or more of the following: a memory (such as number of bytes) needed to store the neural network, a memory (such as number of bytes) needed to temporarily store a decompressed version of the neural network on a temporary memory device such as a Random-Access Memory (RAM), a memory (such as number of bytes) needed to temporarily store a decompressed version of the neural network and intermediate data that is passed on a temporary memory device such as a RAM, a number of layers in a neural network, a number of weights in the neural network, a number of connections in the neural network. The complexity requirement values may be quantized, where the quantization may be uniform or non-uniform.

In an embodiment, a prerequisite_sei_message( ) or input_format_sei_message( ) or alike indicates the picture format to be used as input for the neural network inference, which may comprise, but is not limited to, one or more of the following:
- color primaries, e.g. YCbCr, YCgCo, RGB, GBR, YZX, or XYZ;
- chroma format (e.g. monochrome, 4:2:0, 4:2:2, 4:4:4), bit depth (which may be common for all color components or indicated color-component-wise);
- picture width and height in samples;
- width and height of an effective area, such as a conformance cropping window, within a picture;
- patch width and height in samples for a single neural network inference process;
- color component ordering (e.g. planar or sample-wise interleaved);
- boundary padding mode specifying the padding method to be applied to the patch, when the picture size is not an integer multiple of the patch size (e.g. repeat a picture boundary pixel horizontally and vertically, or wraparound from the right edge of the picture to the left edge, which may be applicable to panoramic images);
- number of input pictures for a neural network inference;
- a normalization mode to be applied to one or more frames that are input to the neural network. One example of normalization mode is a normalization whose result is a normalized frame which has a mean value of zero and a variance value of one; or
- normalizing values, to be used in order to normalize one or more frames that are input to the neural network, according to the normalization mode. For example, a mean value and a standard deviation value.

In an embodiment, an output_format_sei_message( ) or alike indicates the picture format resulting from the neural network inference, which may comprise but is not limited to one or more of the parameters listed above for input_format_sei_message( ).

In an embodiment, a scaling factor flag message, for example, a scaling_factor_flag_sei_message( ) or alike indicates whether the output of the neural network filter is to be scaled. When the flag is set to one, the output of the neural network filter is to be scaled. The scaling operation may comprise multiplying the output of the neural network filter by one or more scaling factors. In one example, the Y, U and V components of a YUV frame that are output by a neural network filter may be scaled by three scaling factors, where each scaling factor sales one of the YUV components. In another example, the Y, U and V components of YUV frame that are output by a neural network filter may be scaled by the same scaling factor.

In an embodiment, a scaling factor message, for example, a scaling_factor_sei_message( ) or alike specifies one or more values to be used for scaling the output of the neural network filter, when the scaling_factor_flag_sei_message( ) indicates that the output of the neural network filter is to be scaled. In another embodiment, the scaling factor flag message may include the one or more values to be used to scale the output of the one or more NNs In an embodiment, a residual filtering flag message, for example, a residual_filtering_flag_sei_message( ) or alike indicates whether the output of the neural network filter is to be added to the input of the neural network filter. When the flag is set to one, the output of the neural network filter is to be added to the input of the neural network filter, and the frame resulting from the addition operation represents the final output of the filtering process. When the scaling_factor_flag_sei_message( ) is set to one, and residual_filtering_flag_sei_message( ) is set to one, the scaling operation indicated by scaling_factor_flag_sei_message( ) may be performed before the addition operation indicated by residual_filtering_flag_sei_message( ).

Still Another Example Embodiment Indicating Pre-Defined Filters

Some neural networks may be de-facto standards for certain purposes or may be selected by a standards-defining organization. For example, an upcoming MPEG Video Coding for Machines standard may define a standard neural network for enhancing decoded frames for an action recognition purpose.

A neural network may be made accessible separately from a video bitstream for which the neural network is applied e.g. for enhancing the decoded pictures reconstructed by decoding the video bitstream. For example, the neural network may be obtained through a Uniform Resource Locator (URL). For example, a Hypertext Transfer Protocol (HTTP) URL for an NNR bitstream may be provided, and a client may request the NNR bitstream by issuing an HTTP GET request for the URL.

It may be beneficial to indicate that a particular (de-facto) standard neural network or a separately provided neural network is in use, rather than having a complete NNR representation of it in the video bitstream.

In an embodiment, the payload of the sei_container( ) comprises an SEI message, which identifies a (de-facto) standard neural network or a separately provided neural network through a reference, such as a Uniform Resource Identifier (URI) (which may be a URL), a universally unique identifier (UUID), or one or more indexes to pre-defined list(s) of known or pre-defined neural networks. Alternatively, the syntax of the SEI message can comprise an NNR bitstream that references an externally specified NN (e.g. NNEF or ONNX). In an embodiment, the sei_container may contain a filter_sei_message( ) whose type identifies that it contains an identifier of a neural network. In an embodiment, an identifier of the neural network is accompanied by a media type (e.g. MIME type) of the neural network in the SEI message. In an embodiment, the identifier and/or the media type of the neural network are directly included in the sei_container as syntax element(s) rather than contained in an SEI message within the sei_container( ).

In an embodiment, a client or alike decodes a sei_container( ) from or along a video bitstream, wherein the decoding comprises decoding one or more purposes and decoding an identifier of a neural network. The client or alike concludes that the one or more purposes are applicable to its needs or tasks. In response to this conclusion, the client or alike fetches the neural network that is identified by the identifier, unless the client or alike already has access to that neural network. Furthermore, in response to this conclusion, the client or alike uses the identified neural network for filtering decoded pictures of the video bitstream.

In addition, it may be beneficial to update the (de-facto) standard NN or the separately provided neural network, e.g. so that it adapts to the content of the video bitstream. In an embodiment, sei_container( ) comprises both i) an SEI message, which identifies a (de-facto) standard neural network or a separately provided neural network through a reference and ii) an update to the identified neural network.

In an embodiment, an update of the neural network is represented by NNR. For example, MPEG NNR version 2 may be used, since MPEG NNR version 2 focuses on compressing weight-updates.

An Example Implementation is Described Below

Add within sei_container( ) another SEI message that specifies which (de-facto) standard NN is used

```
sei_container{
    purpose_sei_message( );
    base_filter_message( );
    filter_sei_message( );
}
```

The SEI message base_filter_message( ) can contain e.g. a UTF8 character string specifying a URI, which identifies the (de-facto) standard NN or a neural network provided separately from the video bitstream.

Another Example Implementation is Described Below

In an embodiment, syntax element(s) in sei_container( ) or in filter_sei_message( ) specify which (de-facto) standard NN or separately provided neural network is used. The syntax element can be e.g. a UTF8 character string specifying a URI, which identifies the (de-facto) standard NN or a separately provided neural network. When null, no 'base' filter is provided through the URI, and the filter_sei_message( ) contains the entire neural network. Alternatively, the syntax can be an NNR bitstream that references an externally specified NN (e.g. NNEF or ONNX).

Yet Another Example Implementation is Described Below:

In sei_container( ), there may be a flag or gating information to indicate the selection of a pre-defined filter or a filter_sei_message( ). However, this may be less extensible than just inferring the operation from the presence of base_filter_message( ) and/or filter_sei_message( ).

In an embodiment, an encoder, a file writer, or alike creates a SEI prefix indication SEI message or alike in or along a video bitstream. The SEI prefix indication SEI message or alike contains an initial part of the content of sei_container( ) that is also in or along the same video bitstream. The SEI prefix indication SEI message or alike may include, for example, the instance(s) of purpose_sei_message( ) and/or the instance(s) of prerequisite_sei_message(s) of the sei_container( ) and/or the instance(s) of base_filter_message( ).

In an embodiment, a file writer or alike encapsulates a video bitstream that contains one or more sei_container( ) structures into a file that conforms to the ISO base media file format. File format storage options for storing either or both of i) SEI prefix indication SEI message(s) or alike that contain an initial part of sei_container( ) and ii) the sei_container( ) structures may include one or more of the following:

Sample Entry. In this option, NN(s) are stored to metadata storage location of the file, e.g. in a MovieBox.

Non-VCL track samples. For enabling random access in playback, sync samples should be aligned among video track(s) containing data of the video bitstream and the non-VCL track. The same non-VCL track can be applied to different video tracks storing data of the same video bitstream or different video bitstreams via track referencing ('tref').

Samples of one or more video tracks containing data of the video bitstream.

In an embodiment, a client or alike (e.g. a decoder, a file reader, or a player) obtains a SEI prefix indication SEI message or alike from or along a video bitstream, the SEI prefix indication SEI message or alike containing an initial part of the content of sei_container( ) that is also in or along the same video bitstream. The client or alike decodes the SEI prefix indication SEI message or alike. Based on the decoded SEI prefix indication SEI message or alike, the client or alike decides one or more of the following: i) whether to fetch the video bitstream, ii) which sei_container ( ) structures are fetched (if any), iii) which NN(s) referenced by sei_container( ) structure(s) are fetched. For example, a SEI prefix indication SEI message or alike may be obtained from an Initialization Segment of a Representation of a non-VCL track that contains sei_container( ) structures for a particular purpose. When the purpose indicated in the SEI prefix indication SEI message or alike matches the client's need or task, the client may determine to fetch the representation of the non-VCL track that contains the respective sei_container( ) structures.

Signaling the purpose of one or more neural networks has multiple benefits, including but not limited to i) being able to select which neural network among multiple available ones is applicable for the need(s) or task(s) of the client or alike; ii) fetching only selected neural network(s) among multiple available ones, thus reducing the required network bandwidth and transmission time for obtaining the needed neural network(s); iii) executing the inference only for the selected neural network(s), thus reducing computations and power consumption.

Embodiments Describing In-Loop Decoding Dependency

The following embodiments involve a normative decoding dependency, and may be used when the neural network is within the decoding loop, in either end-to-end learned codec or a NN-enhanced conventional codec (such as H.266/VVC with a NN in-loop filter, also may be referred as a hybrid codec approach).

In an embodiment, a dedicated NAL unit including information, as described above in one or more SEI-based embodiments, is proposed.

Figure 13:
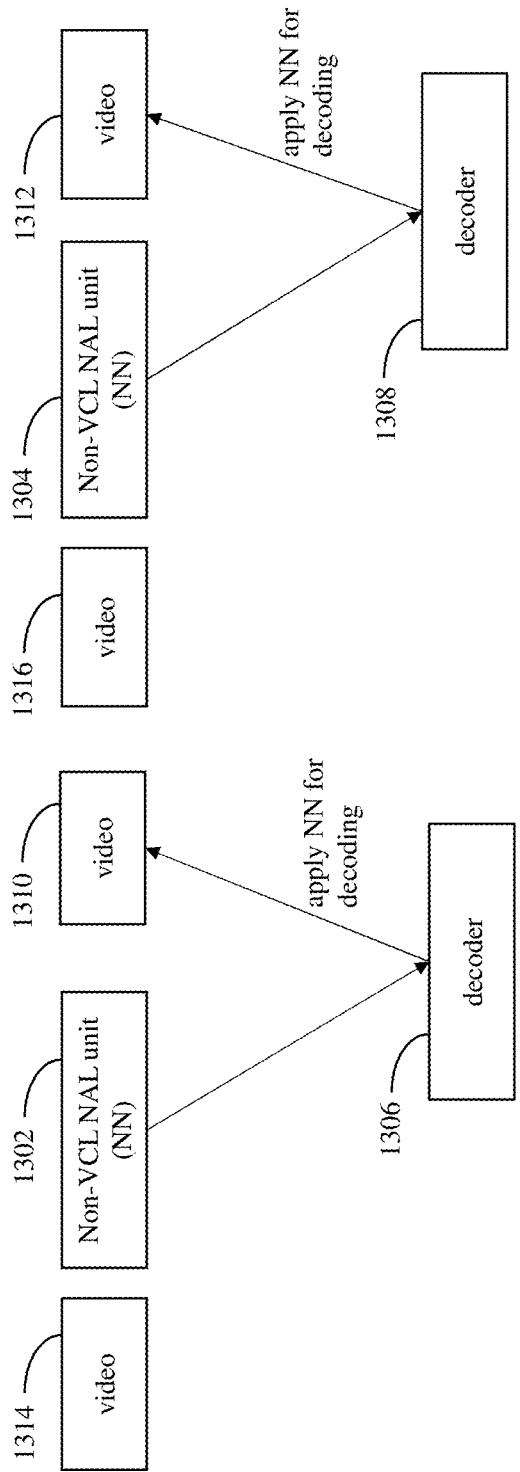
FIG. 13 illustrates a media bitstream obtained based on normative decoding dependency, in accordance with an embodiment.

Referring to FIG. 13, it illustrates a video bitstream in accordance with normative decoding dependency, in accordance with an embodiment. The neural network is signaled within the video bitstream, for example, inside non-VCL NAL (NN NAL) units 1302 and 1304. The neural network (or an update of a neural network) is extracted from the NN NAL units 1302 and 1304 to decode one or more units of video bitstream 1310, 1312 (e.g. VCL NAL units or coded video frames), by using one or more decoders, for example, decoders 1306 and 1308 to get decoded video. Video 1346 and 1316 may be decoded using a 'default' decoder configuration, for example, by using the pretrained neural network, or by using the latest updated neural network (it depends on the persistence scope of the previously signaled NN or NN update).

Embodiments described for SEI message(s) apply similarly to the NN NAL unit too. The NN NAL unit may be regarded as, or may comprise, the sei_container( ) structure in its entirety or partly in different embodiments, and the SEI NAL units contained in sei_container( ) may be called differently but may have similar structure. When an NN NAL unit is in use, the filtering performed by the NN NAL unit may be considered mandatory for decoders and may be used to filter decoded pictures that may be subsequently used as reference pictures for predicting other pictures. In addition to or instead of filtering, the NN NAL units may specify other neural network based decoding operations, such as intra prediction, inter prediction, or transform.

In some embodiments, more than one NN may be available for performing decoding operation. When more than one NNs are available, an NN may need to be identified or addressed separately or explicitly (e.g. through IDs) so that a correct NN is used in a decoding operation.

The validity of a NN NAL unit may be defined similarly to parameter sets. A NN NAL unit should be available to the decoder before being referenced.

In an embodiment, the NN may be signalled as part of a parameter set. For example, a new APS type may be defined for a video coding standard such as VVC. In other words, an NN NAL unit may be an adaptation parameter set NAL unit with an APS type indicating NN filtering. In an example embodiment, the following syntax may be used for an APS:

| | Descriptor |
|---|---|
| adaptation_parameter_set_rbsp( ) { | |
|   aps_params_type | u(3) |
|   aps_adaptation_parameter_set_id | u(5) |
|   aps_chroma_present_flag | u(1) |
|   if( aps_params_type = = ALF_APS ) | |
|     alf_data( ) | |
|   else if( aps_params_type = = LMCS_APS ) | |
|     lmcs_data( ) | |
|   else if( aps_params_type = = SCALING_APS ) | |
|     scaling_list_data( ) | |

| | Descriptor |
|---|---|
| else if( aps_params_type = = NN_APS ) | |
|   nn_data( ) | |
|   aps_extension_flag | u(1) |
|   if( aps_extension_flag ) | |
|     while( more_rbsp_data( ) ) | |
|       aps_extension_data_flag | u(1) |
|   rbsp_trailing_bits( ) | |
| } | |

NN_APS may be a pre-defined constant value, e.g. equal to 3.

In an embodiment, nn_data( ) is an NNR bitstream.

In an embodiment, nn_data( ) has syntax, semantics and child syntax structures like those of sei_container( ). However, it may be noted that the syntax structures within nn_data( ) do not necessarily comply with the SEI message syntax.

In an embodiment, nn_data( ) comprises syntax and semantics like those of filter_sei_message( ) although it should be noticed that the syntax structures within nn_data ( ) do not necessarily comply with the SEI message syntax.

In an embodiment, nn_data( ) comprises syntax and semantics comprising a combination of base_filter_message ( ) and filter_sei_message( ), although it may be noted that the syntax structures within nn_data( ) do not necessarily comply with the SEI message syntax. In this embodiment, a the nn_data( ) may comprise one or both of a reference or an identifier, such as a URI, that identifies a (de-facto) standard neural network or a separately provided neural network, and an update of the identified neural network.

APSs have IDs, thus it is possible to refer to a previous APS. However, APS as specified in VVC does not allow partial updates or predictively coded updates, but rather an APS of a particular type and ID always overrides the previous APS with the same type and ID.

In an embodiment, one or more NNs that are or may be applied for decoding are indicated through their identifiers or alike, such as APS IDs, in a syntax structure of video bitstream, such as a slice header, a picture header, or a picture parameter set. The scope of the syntax structure may define the parts of the video for which the one or more NNs are or may be applied. For example, when one or more NN identifiers are included in a slice header, they respective one or more NNs are or may be applied for the respective slice. When more than one NN is indicated to be applicable, the selection which NN is applied may be performed block-wise, such as CTU-wise in H.266/VVC. An encoder may encode block-wise, into the bitstream, an entropy-coded index to the list of NNs (whose IDs are listed e.g. in a slice header), and respectively a decoder may decode block-wise, from the bitstream, an entropy-coded index to the list of identified NNs.

In an embodiment, a file writer or alike encapsulates a video bitstream that contains NN APS(s) into a file that conforms to the ISO base media file format. File format storage options for APS based NN signaling may include one or more of the following:
- Sample Entry. In this option, NN(s) are stored to metadata storage location of the file, e.g., in the MovieBox.
- Non-VCL track samples. For enabling random access in playback, sync samples should be aligned among video track(s) containing data of the video bitstream and the non-VCL track. The same non-VCL track can be applied to different video tracks storing data of the same video bitstream or different video bitstreams via track referencing ('tref').
- Samples of one or more video tracks containing data of the video bitstream.

NN data may be stored in the NNR bitstream syntax format, which is a serialized stream of NNR units as defined in MPEG specification ISO/IEC 15938-17, for example:
- Compressed neural network bitstream in the form of NNR units, also containing specific NNR units that carry the neural network topology information;
- Compressed neural network bitstream in the form of NNR units, also containing specific NNR units that reference the neural network topology information as external reference such as a URL/URI, ID or alike. Such an ID may be defined or specified and enumerated in another specification or known information source (specification, web service, web page, AP and alike);

In an example, in NNR units of type MPS or similar parameter set related NNR units, the neural network and related parameters with a single unique ID that represents the NN and flags for default parameter usage can be signaled, which could be like a codebook. The contents of the MPS in such a signaling can be as in the following syntax example where:
- mps_NN_enum_id may signal the enumeration id of the NN being utilized. This id may be defined and signaled by another information source (e.g. another specification, a web service, a web page or resource, an SEI message, etc.)
- mps_NN_default_params_flag may signal the utilization of default configuration parameters for the NN
- NN_params( ) may contain non-default configuration parameters
- NN_params_enum_id may indicate an enumeration id, a URI/URL or any unique identifier for the NN and/or NN parameters so that signaling only this enumeration may be sufficient to configure the NN.

The other syntax elements are as defined in ISO/IEC 15938-17 specification.

| | Descriptor |
|---|---|
| nnr_model_parameter_set_payload( ) { | |
|   topology_carriage_flag | u(1) |
|   mps_sparsification_flag | u(1) |
|   mps_pruning_flag | u(1) |
|   mps_unification_flag | u(1) |
|   mps_decomposition_performance_map_flag | u(1) |
|   mps_quantization_method_flags | u(3) |
|   mps_NN_enum_id | st(v) or any type |
|   mps_NN_default_params_flag | u(1) |
|   mps_NN_param_enum_present_flag | u(1) |
|   reserved | u(6) |
|   if (!mps_NN_default_params_flag) { | |

-continued

| | Descriptor |
|---|---|
| if(mps_NN_param_enum_present_flag) { | |
|     NN_params_enum_id | st(v) or any type |
| } else { | |
|     NN_params( ) | st(v) or any type |
|     } | |
|   } | |
| } | |
| if((mps_quantization_method_flags & NNR_QSU) == NNR_QSU \|\| (mps_quantization_method_flags & NNR_QCB) == NNR_QCB) { | |
|   mps_qp_density | u(3) |
|   mps_quantization_parameter | i(13) |
| } | |
| if(mps_sparsification_flag == 1) | |
|   sparsification_performance_map( ) | |
| if(mps_pruning_flag == 1) | |
|   pruning_performance_map( ) | |
| if(mps_unification_flag == 1) | |
|   unification_performance_map( ) | |
| if(mps_decomposition_performance_map_flag == 1) | |
|   decomposition_performance_map( ) | |
| } | |

In another embodiment, in the nn_data( ) of an APS, the following may be signaled

| | Descriptor |
|---|---|
| nn_data( ) { | |
|   mps_NN_enum_id | st(v) or any type |
|   mps_NN_default_params_flag | u(1) |
|   mps_NN_param_enum_present_flag | u(1) |
|   reserved | u(6) |
|   if (!mps_NN_default_params_flag) { | |
|     if(mps_NN_param_enum_present_flag) { | |
|       NN_params_enum_id | st(v) or any type |
|     } else { | |
|       NN_params( ) | st(v) or any type |
|     } | |
|   } | |
| } | |

When nn_data( ) is parsed, NN related enumerations and parameters may be obtained by the parser and then passed on to the necessary process which will initialize and use the NN in decoding/post-preprocessing operations.

Some Additional Embodiments are Described Below

While embodiments were described in relation to video bitstreams, they generally apply to any media types with SEI or alike. e.g. MPEG Visual Volumetric Video-based Coding (V3C, ISO/IEC 23090-5) has an SEI mechanism.

sei_container( ) may be utilized in audio encoded bitstreams such as MPEG audio bitstreams as an extension such as syntax elements that contain user data and/or as profile indicators which indicate the presence of such data in the bitstream. There may be multiple such sei_containers per each audio channel.

In an embodiment, enumerating the topology may be applied as follows:

The decoder-side device may already have a set of N possible topologies of neural networks. Topology here refers to the structure or architecture of the neural networks, such as number of layers, types of layers, number of computational units per layer, number of convolutional channels per layer, hyper-parameters of the layers, and the like. Topology information usually does not include the values of the weights and of other learnable parameters. Computational units may be referred to as artificial neurons. Artificial neurons are computation units that form a fully-connected layer.

For each topology, the decoder-side device may have the associated weights and other learnable parameters. These weights may be shared among two or more different topologies.

In one embodiment, the encoder-side device may signal information about which topology is to be used. The decoder-side device would then use that topology and the associated weights.

In one embodiment, the signaled information may be a unique identifier (ID). The encoder-side device and the decoder-side devices are assumed to have a look-up table which associates the ID to the corresponding topology. The ID may be signaled within the NNR_TPL unit of the high-level syntax of MPEG-NNR standard. The MPEG-NNR bitstream would be signaled within filter_sei_message( ).

In another embodiment, the signaled information may be a full representation of a neural network topology. For example, it may be a subset of a topology already present at decoder side (e.g., a subset of layers), and only weights associated to the subset of the topology are selected at decoder side.

It is remarked that the design is not limited to neural network based filters, but is also applicable to any types of filtering, including for example adaptive loop filtering, which may be identical or similar to that specified in H.266/VVC. In an embodiment, sei_container( ) may contain any type of filter_sei_message( ), for example, filter_sei_message( ) does not necessarily specify a neural network based filter but could specify any filter, such as an adaptive loop filter (ALF), e.g. as specified in H.266/VVC but applying as a post-processing operation (not affecting reconstruction of reference pictures). In an embodiment, different types of sei_container( ) structures are specified, where one or more types may indicate a neural network based filter and another one or more types may indicate other type(s) of filter(s), such as an adaptive loop filter. For example, sei_container( ) may be an SEI message whose payload type indicates which type of a filter is specified by the SEI message.

In an embodiment, a filter is specified or identified in a parameter set, such as an adaptation parameter set. The filter may, for example, be a neural network based filter or an adaptive loop filter as described in other embodiments. Furthermore, sei_container( ) contains a filter_sei_message ( ) or alike that identifies the parameter set that contains or identifies the filter. sei_container may contain other structures, such as purpose_sei_message( ) as described in other embodiments. Thus, this embodiment enables the signaling of the filter in a parameter set and associating the signaled filter to a purpose in sei_container( ), which may for example be contained in an SEI NAL unit. For example, an ALF filter may be specified using an ALF APS and referenced by sei_container( ) for filtering taking place as a post-processing operation. It may be more efficient in byte count to contain NNR bitstreams in parameter sets than SEI messages due to the way of expressing payloadSize of an SEI message.

In an embodiment, sei_container( ) and/or the contained SEI messages may indicate which contained SEI messages are mandatory to be processed in order to perform the filtering. Some contained SEI messages may be marked optional, for example, when they provide information or describe filtering steps of minor importance.

Figure 14:
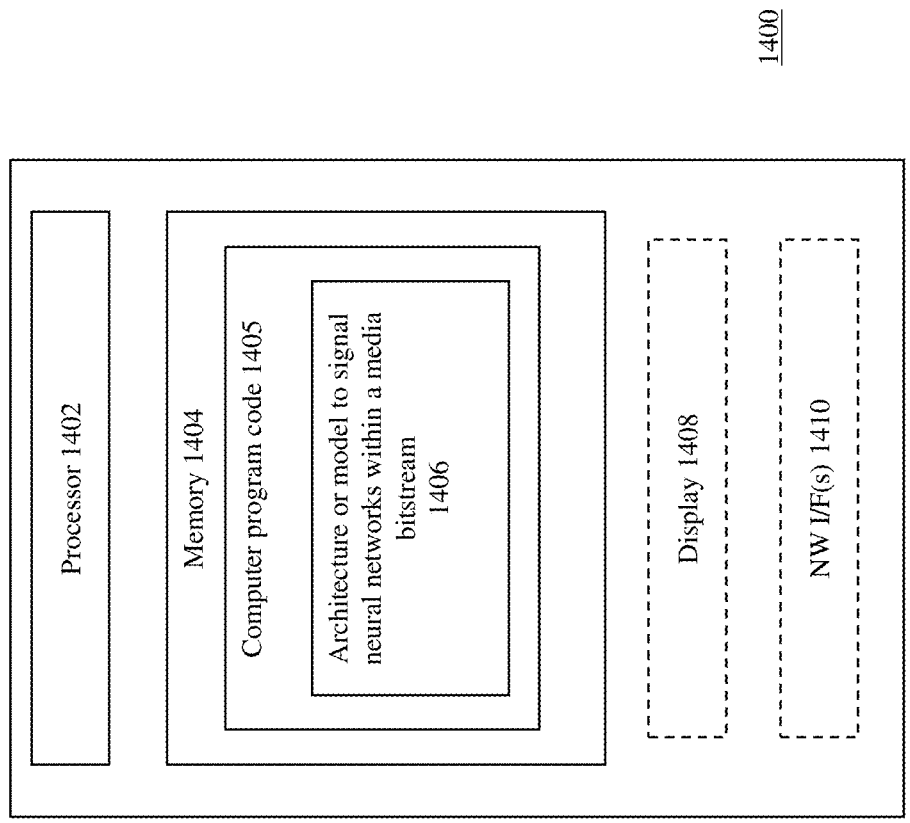
FIG. 14 is an example apparatus configured to signal neural networks within a media bitstream, in accordance with an embodiment.

FIG. 14 is an example apparatus 1400, which may be implemented in hardware, configured to signal neural networks within a media bitstream, based on the examples described herein. Some example of the apparatus 1400 include, but are not limited to, the apparatus 50, the client device 604, and the apparatus 700. The apparatus 1400 comprises a processor 1402, at least one non-transitory memory 1404 including a computer program code 1405, wherein the at least one memory 1404 and the computer program code 1405 are configured to, with the at least one processor 1402, cause the apparatus 1400 to signal neural networks within a media bitstream 1406 based on the examples described herein. The apparatus 1400 optionally includes a display 1408 that may be used to display content during rendering. The apparatus 1400 optionally includes one or more network (NW) interfaces (I/F(s)) 1410. The NW I/F(s) 1410 may be wired and/or wireless and communicate over the Internet/other network(s) via any communication technique. The NW I/F(s) 1410 may comprise one or more transmitters and one or more receivers.

FIG. 15 is an example method 1500 to receive a neural network within a media bitstream, in accordance with an embodiment. At 1502, the method includes receiving a media bitstream including one or more media units and a first enhancement information message. The first enhancement information message includes at least two independently parsable structures, for example, a first independently parsable structure including information about at least one purpose of one or more neural networks (NNs) to be applied to the one or more media units, and a second independently parsable structure including or identifying the one or more neural networks. An example of the first enhancement information message include an NN supplemental enhancement information message. In an embodiment, the first enhancement information message is included in an enhancement information container. An example of the one or more media units include one or more video units, where an example of the one or more video units include one or more network abstraction layer video units.

At 1504, the method includes decoding the one or more media units. At 1506, the method includes using the one or more neural networks to enhance or filter one or more frames of the decoded one or more media units, based on the at least one purpose. In an example, the apparatus 1400 may be used to implement the method 1500.

FIG. 16 is an example method 1600 to signal neural network within a media bitstream, in accordance with another embodiment. At 1602, the method includes encoding a media bitstream including one or more media units and a first enhancement information message. The first enhancement information message includes at least two independently parsable structures, for example, a first independently parsable structure comprising information about at least one purpose of one or more neural networks (NNs) to be applied to the one or more media units, and a second independently parsable structure comprising or identifying the one or more neural networks. At 1604, the method includes signaling the media bitstream to a decoder-side device, where the one or more neural networks are intended to be used for the at least one purpose used to enhance or filter one or more frames of the decoded one or more media units. In an example, the apparatus 1400 may be used to implement the method 1600.

Figure 17:
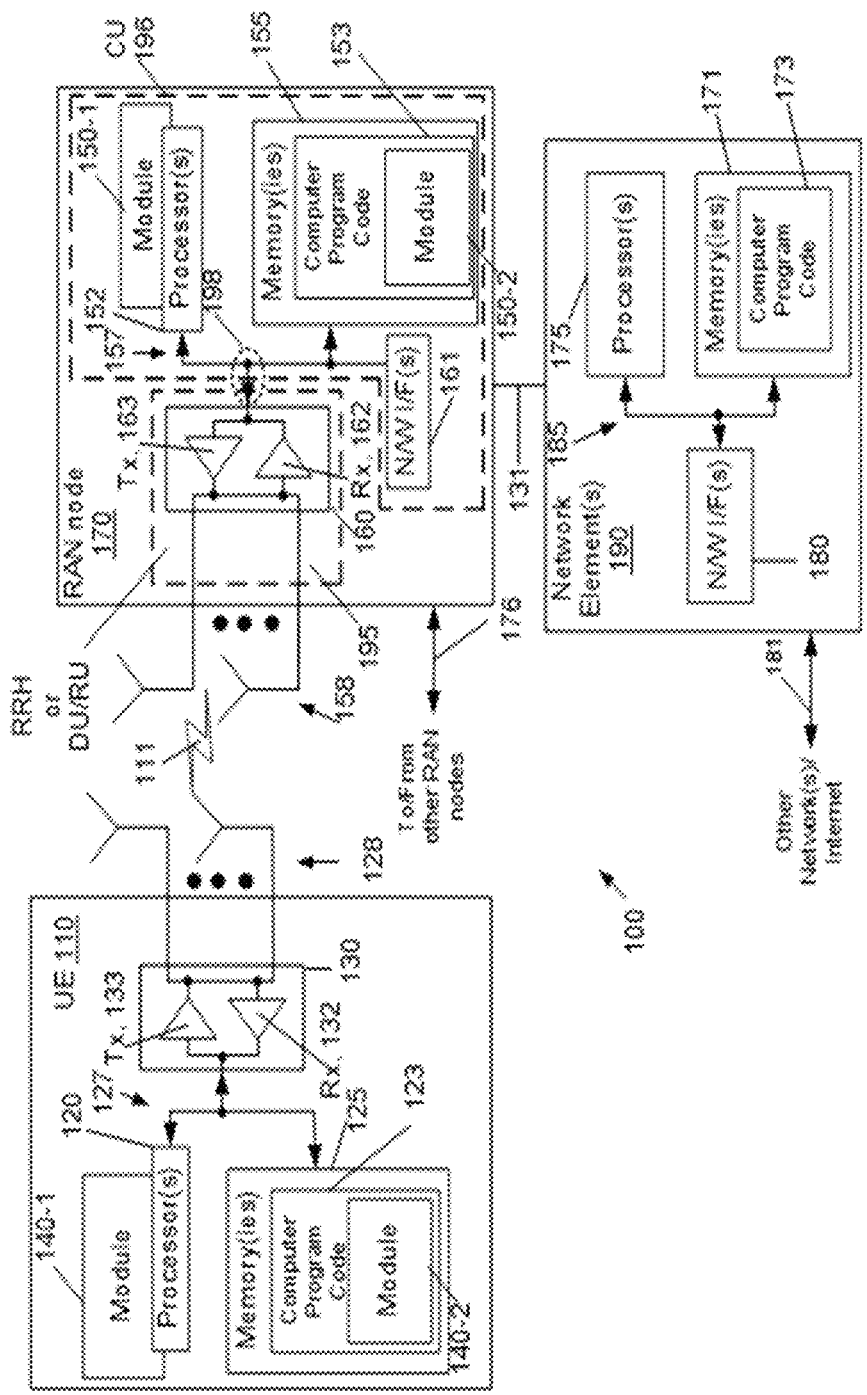
FIG. 17 is a block diagram of one possible and non-limiting system in which the example embodiments may be practiced.

Turning to FIG. 17, this figure shows a block diagram of one possible and non-limiting example in which the examples may be practiced. A user equipment (UE) 110, radio access network (RAN) node 170, and network element(s) 190 are illustrated. In the example of FIG. 1, the user equipment (UE) 110 is in wireless communication with a wireless network 100. A UE is a wireless device that can access the wireless network 100. The UE 110 includes one or more processors 120, one or more memories 125, and one or more transceivers 130 interconnected through one or more buses 127. Each of the one or more transceivers 130 includes a receiver, Rx, 132 and a transmitter, Tx, 133. The one or more buses 127 may be address, data, or control buses, and may include any interconnection mechanism, such as a series of lines on a motherboard or integrated circuit, fiber optics or other optical communication equipment, and the like. The one or more transceivers 130 are connected to one or more antennas 128. The one or more memories 125 include computer program code 123. The UE 110 includes a module 140, comprising one of or both parts 140-1 and/or 140-2, which may be implemented in a number of ways. The module 140 may be implemented in hardware as module 140-1, such as being implemented as part of the one or more processors 120. The module 140-1 may be implemented also as an integrated circuit or through other hardware such as a programmable gate array. In another example, the module 140 may be implemented as module 140-2, which is implemented as computer program code 123 and is executed by the one or more processors 120. For instance, the one or more memories 125 and the computer program code 123 may be configured to, with the one or more processors 120, cause the user equipment 110 to perform one or more of the operations as described herein. The UE 110 communicates with RAN node 170 via a wireless link 111.

The RAN node 170 in this example is a base station that provides access by wireless devices such as the UE 110 to the wireless network 100. The RAN node 170 may be, for example, a base station for 5G, also called New Radio (NR). In 5G, the RAN node 170 may be a NG-RAN node, which is defined as either a gNB or an ng-eNB. A gNB is a node providing NR user plane and control plane protocol terminations towards the UE, and connected via the NG interface to a 5GC (such as, for example, the network element(s) 190). The ng-eNB is a node providing E-UTRA user plane and control plane protocol terminations towards the UE, and connected via the NG interface to the 5GC. The NG-RAN node may include multiple gNBs, which may also include a central unit (CU) (gNB-CU) 196 and distributed unit(s) (DUs) (gNB-DUs), of which DU 195 is shown. Note that the DU may include or be coupled to and control a radio unit (RU). The gNB-CU is a logical node hosting radio resource control (RRC), SDAP and PDCP protocols of the gNB or RRC and PDCP protocols of the en-gNB that controls the operation of one or more gNB-DUs. The gNB-CU terminates the F1 interface connected with the gNB-DU. The F1 interface is illustrated as reference 198, although reference 198 also illustrates a link between remote elements of the RAN node 170 and centralized elements of the RAN node 170, such as between the gNB-CU 196 and the gNB-DU 195. The gNB-DU is a logical node hosting RLC, MAC and PHY layers of the gNB or en-gNB, and its operation is partly controlled by gNB-CU. One gNB-CU supports one or multiple cells. One cell is supported by only one gNB-DU. The gNB-DU terminates the F1 interface 198 connected with the gNB-CU. Note that the DU 195 is considered to include the transceiver 160, for example, as part of a RU, but some examples of this may have the transceiver 160 as part of a separate RU, for example, under control of and connected to the DU 195. The RAN node 170 may also be an eNB (evolved NodeB) base station, for LTE (long term evolution), or any other suitable base station or node.

The RAN node 170 includes one or more processors 152, one or more memories 155, one or more network interfaces (N/W I/F(s)) 161, and one or more transceivers 160 interconnected through one or more buses 157. Each of the one or more transceivers 160 includes a receiver, Rx, 162 and a transmitter, Tx, 163. The one or more transceivers 160 are connected to one or more antennas 158. The one or more memories 155 include computer program code 153. The CU 196 may include the processor(s) 152, memories 155, and network interfaces 161. Note that the DU 195 may also contain its own memory/memories and processor(s), and/or other hardware, but these are not shown.

The RAN node 170 includes a module 150, comprising one of or both parts 150-1 and/or 150-2, which may be implemented in a number of ways. The module 150 may be implemented in hardware as module 150-1, such as being implemented as part of the one or more processors 152. The module 150-1 may be implemented also as an integrated circuit or through other hardware such as a programmable gate array. In another example, the module 150 may be implemented as module 150-2, which is implemented as computer program code 153 and is executed by the one or more processors 152. For instance, the one or more memories 155 and the computer program code 153 are configured to, with the one or more processors 152, cause the RAN node 170 to perform one or more of the operations as described herein. Note that the functionality of the module 150 may be distributed, such as being distributed between the DU 195 and the CU 196, or be implemented solely in the DU 195.

The one or more network interfaces 161 communicate over a network such as via the links 176 and 131. Two or more gNBs 170 may communicate using, for example, link 176. The link 176 may be wired or wireless or both and may implement, for example, an Xn interface for 5G, an X2 interface for LTE, or other suitable interface for other standards.

The one or more buses 157 may be address, data, or control buses, and may include any interconnection mechanism, such as a series of lines on a motherboard or integrated circuit, fiber optics or other optical communication equipment, wireless channels, and the like. For example, the one or more transceivers 160 may be implemented as a remote radio head (RRH) 195 for LTE or a distributed unit (DU) 195 for gNB implementation for 5G, with the other elements of the RAN node 170 possibly being physically in a different location from the RRH/DU, and the one or more buses 157 could be implemented in part as, for example, fiber optic cable or other suitable network connection to connect the other elements (for example, a central unit (CU), gNB-CU) of the RAN node 170 to the RRH/DU 195. Reference 198 also indicates those suitable network link(s).

It is noted that description herein indicates that 'cells' perform functions, but it should be clear that equipment which forms the cell may perform the functions. The cell makes up part of a base station. That is, there can be multiple cells per base station. For example, there could be three cells for a single carrier frequency and associated bandwidth, each cell covering one-third of a 360 degree area so that the single base station's coverage area covers an approximate oval or circle. Furthermore, each cell can correspond to a single carrier and a base station may use multiple carriers. So, when there are three 120 degree cells per carrier and two carriers, then the base station has a total of 6 cells.

The wireless network 100 may include a network element or elements 190 that may include core network functionality, and which provides connectivity via a link or links 181 with a further network, such as a telephone network and/or a data communications network (for example, the Internet). Such core network functionality for 5G may include access and mobility management function(s) (AMF(S)) and/or user plane functions (UPF(s)) and/or session management function(s) (SMF(s)). Such core network functionality for LTE may include MME (Mobility Management Entity)/SGW (Serving Gateway) functionality. These are merely example functions that may be supported by the network element(s) 190, and note that both 5G and LTE functions might be supported. The RAN node 170 is coupled via a link 131 to the network element 190. The link 131 may be implemented as, for example, an NG interface for 5G, or an S1 interface for LTE, or other suitable interface for other standards. The network element 190 includes one or more processors 175, one or more memories 171, and one or more network interfaces (N/W I/F(s)) 180, interconnected through one or more buses 185. The one or more memories 171 include computer program code 173. The one or more memories 171 and the computer program code 173 are configured to, with the one or more processors 175, cause the network element 190 to perform one or more operations.

The wireless network 100 may implement network virtualization, which is the process of combining hardware and software network resources and network functionality into a single, software-based administrative entity, a virtual network. Network virtualization involves platform virtualization, often combined with resource virtualization. Network virtualization is categorized as either external, combining many networks, or parts of networks, into a virtual unit, or internal, providing network-like functionality to software containers on a single system. Note that the virtualized entities that result from the network virtualization are still implemented, at some level, using hardware such as processors 152 or 175 and memories 155 and 171, and also such virtualized entities create technical effects.

The computer readable memories 125, 155, and 171 may be of any type suitable to the local technical environment and may be implemented using any suitable data storage technology, such as semiconductor based memory devices, flash memory, magnetic memory devices and systems, optical memory devices and systems, fixed memory and removable memory. The computer readable memories 125, 155, and 171 may be means for performing storage functions. The processors 120, 152, and 175 may be of any type suitable to the local technical environment, and may include one or more of general purpose computers, special purpose computers, microprocessors, digital signal processors (DSPs) and processors based on a multi-core processor architecture, as non-limiting examples. The processors 120, 152, and 175 may be means for performing functions, such as controlling the UE 110, RAN node 170, network element(s) 190, and other functions as described herein.

In general, the various embodiments of the user equipment 110 can include, but are not limited to, cellular telephones such as smart phones, tablets, personal digital assistants (PDAs) having wireless communication capabilities, portable computers having wireless communication capabilities, image capture devices such as digital cameras having wireless communication capabilities, gaming devices having wireless communication capabilities, music storage and playback appliances having wireless communication capabilities, Internet appliances permitting wireless Internet access and browsing, tablets with wireless communication capabilities, as well as portable units or terminals that incorporate combinations of such functions.

One or more of modules 140-1, 140-2, 150-1, and 150-2 may be configured to signal neural networks within a media bitstream of neural networks based on the examples described herein. Computer program code 173 may also be configured to signal neural networks within a media bitstream based on the examples described herein.

As described above, FIGS. 15 and 16 include flowcharts of an apparatus (e.g. 50, 100, 604, 700, or 1400), method, and computer program product according to certain example embodiments. It will be understood that each block of the flowcharts, and combinations of blocks in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory (e.g. 58, 125, 704, or 1404) of an apparatus employing an embodiment of the present invention and executed by processing circuitry (e.g. 56, 120, 702 or 1402) of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

A computer program product is therefore defined in those instances in which the computer program instructions, such as computer-readable program code portions, are stored by at least one non-transitory computer-readable storage medium with the computer program instructions, such as the computer-readable program code portions, being configured, upon execution, to perform the functions described above, such as in conjunction with the flowcharts of FIGS. 15 and 16. In other embodiments, the computer program instructions, such as the computer-readable program code portions, need not be stored or otherwise embodied by a non-transitory computer-readable storage medium, but may, instead, be embodied by a transitory medium with the computer program instructions, such as the computer-readable program code portions, still being configured, upon execution, to perform the functions described above.

Accordingly, blocks of the flowcharts support combinations of means for performing the specified functions and combinations of operations for performing the specified functions for performing the specified functions. It will also be understood that one or more blocks of the flowcharts, and combinations of blocks in the flowcharts, may be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

In the above, some example embodiments have been described with reference to an SEI message or an SEI NAL unit. It needs to be understood, however, that embodiments can be similarly realized with any similar structures or data units. Where example embodiments have been described with SEI messages contained in a structure, any independently parsable structures could likewise be used in embodiments. Specific SEI NAL unit and a SEI message syntax structures have been presented in example embodiments, but it needs to be understood that embodiments generally apply to any syntax structures with a similar intent as SEI NAL units and/or SEI messages.

In the above, some embodiments have been described in relation to a particular type of a parameter set (namely adaptation parameter set). It needs to be understood, however, that embodiments could be realized with any type of parameter set or other syntax structure in the bitstream.

In the above, some example embodiments have been described with the help of syntax of the bitstream. It needs to be understood, however, that the corresponding structure and/or computer program may reside at the encoder for generating the bitstream and/or at the decoder for decoding the bitstream.

In the above, where example embodiments have been described with reference to an encoder, it needs to be understood that the resulting bitstream and the decoder have corresponding elements in them. Likewise, where example embodiments have been described with reference to a decoder, it needs to be understood that the encoder has structure and/or computer program for generating the bitstream to be decoded by the decoder.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Accordingly, the description is intended to embrace all such alternatives, modifications and variances which fall within the scope of the appended claims. Although specific terms are employed herein, they are used in a generic and descriptive sense only and not for purposes of limitation.

It should be understood that the foregoing description is only illustrative. Various alternatives and modifications may be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A method comprising:
receiving a media bitstream comprising one or more media units and a container, wherein the container comprises at least a first enhancement information message and a second enhancement information message, wherein the first enhancement information message comprises or identifies a neural network, and the second enhancement information message comprises an update to the neural network;
wherein the received media bitstream comprises a third enhancement information message;
decoding the one or more media units;
updating the neural network based on the update; and
using the updated neural network to enhance or filter the decoded one or more media units within a temporal scope determined with the third enhancement information message, a spatial scope determined with the third enhancement information message, or a spatio-temporal scope determined with the third enhancement information message, wherein the third enhancement information message indicates that the updated neural network is active for use.

2. The method of claim 1, wherein the update to the neural network is represented by a neural network representation bitstream.

3. The method of claim 1, wherein the container comprises a supplemental enhancement information (SEI) network abstraction layer (NAL) unit and the first and second enhancement information messages comprise SEI messages.

4. The method of claim 3, wherein the container comprises an identifier for the neural network, and the method further comprises:
receiving within the media bitstream a filter activation SEI message comprising the identifier for the neural network, wherein the filter activation SEI message indicates activation of the neural network identified by the identifier within the temporal scope determined by the filter activation SEI message, the spatial scope determined by the filter activation SEI message, or the spatio-temporal scope determined by the filter activation SEI message, wherein the third enhancement information message comprises the filter activation SEI message.

5. The method of claim 1, wherein the temporal scope, the spatial scope or the spatio-temporal scope comprises:
first one or more frames of the decoded one or more media units, or
one or more areas within second one or more frames of the decoded one or more media units.

6. A method comprising:
encoding a media bitstream comprising one or more media units and a container;
encoding, within the container, at least a first enhancement information message and a second enhancement information message;
encoding, within the media bitstream, a third enhancement information message;
encoding, within the first enhancement information message, a neural network or an identification of the neural network; and
encoding, within the second enhancement information message, an update to the neural network, wherein:
the update to the neural network is intended to be used for updating the neural network; and
the updated neural network is intended to be active and used to enhance or filter decoded one or more media units within a temporal scope determined with the third enhancement information message, a spatial scope determined with the third enhancement information message, or a spatio-temporal scope determined with the third enhancement information message, wherein the third enhancement information message indicates that the updated neural network is active for use.

7. The method of claim 6, wherein the update to the neural network is represented by a neural network representation bitstream.

8. The method of claim 6, wherein the container comprises a supplemental enhancement information (SEI) network abstraction layer (NAL) unit and the first and second enhancement information messages comprise SEI messages.

9. The method of claim 8, further comprising:
encoding, within the container, an identifier for the neural network;
encoding, within the media bitstream, a filter activation SEI message;
wherein the third enhancement information message encoded within the media bitstream comprises the filter activation SEI message;
encoding, within the filter activation SEI message, the identifier for the neural network; and
indicating, within the filter activation SEI message, activation of the neural network identified by the identifier within the temporal scope determined by the filter activation SEI message, the spatial scope determined by the filter activation SEI message, or the spatio-temporal scope determined by the filter activation SEI message.

10. The method of claim 6, wherein the temporal scope, the spatial scope, or the spatio-temporal scope comprises:
first one or more frames of the decoded one or more media units, or
one or more areas within second one or more frames of the decoded one or more media units.

11. The method of claim 6, further comprising:
encoding, within the bitstream, a reference that specifies that the first enhancement information message specifies the neural network, or that the second enhancement information message specifies the update to the neural network.

12. An apparatus comprising:
at least one processor; and
at least one non-transitory memory storing instructions that, when executed by the at least one processor, cause the apparatus at least to:
receive a media bitstream comprising one or more media units and a container, wherein the container comprises at least a first enhancement information message and a separate second enhancement information message, wherein the first enhancement information message comprises or identifies a neural network, and the second enhancement information message comprises an update to the neural network;
wherein the received media bitstream comprises a third enhancement information message;
decode the one or more media units;
update the neural network based on the update; and
use the updated neural network to enhance or filter the decoded one or more media units within a temporal scope determined with the third enhancement information message, a spatial scope determined with the third enhancement information message, or a spatio-temporal scope determined with the third enhancement information message, wherein the third enhancement information message indicates that the updated neural network is active for use.

13. The apparatus of claim 12, wherein the instructions, when executed by the at least one processor, cause the apparatus at least to:
receive, within the bitstream, a uniform resource identifier that identifies the update to the neural network or the neural network.

14. The apparatus of claim 12, wherein the updating the neural network based on the update is performed when the update to the neural network and the neural network are both identified with the uniform resource identifier.

15. The apparatus of claim 14, wherein the container comprises a supplemental enhancement information (SEI) network abstraction layer (NAL) unit and the first and second enhancement information messages comprise SEI messages, wherein the container comprises an identifier for the neural network, and the apparatus is further caused to:
receive within the media bitstream a filter activation SEI message comprising the identifier for the neural network, wherein the filter activation SEI message indicates activation of the neural network identified by the identifier within the temporal scope determined by the filter activation SEI message, the spatial scope determined by the filter activation SEI message, or the spatio-temporal scope determined by the filter activation SEI message, wherein the third enhancement information message comprises the filter activation SEI message.

16. The apparatus of claim 12, wherein the temporal scope, the spatial scope, or the spatio-temporal scope comprises:
first one or more frames of the decoded one or more media units, or
one or more areas within second one or more frames of the decoded one or more media units.

17. The apparatus of claim 12, wherein the instructions, when executed by the at least one processor, cause the apparatus at least to:
receive, within the media bitstream, a first neural network identifier that identifies the update to the neural network or the neural network;
wherein the updating the neural network based on the update is performed when the update to the neural network and the neural network are both identified with the first neural network identifier; and
receive, within the media bitstream, a second neural network identifier associated with the third enhancement information message; and
wherein the updated neural network used to enhance or filter the decoded one or more media units within the temporal scope determined with the third enhancement information message, the spatial scope determined with the third enhancement information message, or the spatio-temporal scope determined with the third enhancement information message is further identified by the second neural network identifier.

18. The apparatus method of claim 12, wherein:
the update to the neural network is represented by a neural network representation bitstream; and
the neural network representation bitstream conforms to ISO/IEC 15938-17.

19. An apparatus comprising:
at least one processor; and
at least one non-transitory memory storing instructions that, when executed by the at least one processor, cause the apparatus at least to:
encode a media bitstream comprising one or more media units and a container;
encode, within the container, at least a first enhancement information message and a second enhancement information message;
encode, within the media bitstream, a third enhancement information message;
encode, within the first enhancement information message, a neural network or an identification of the neural network; and
encode, within the second enhancement information message, an update to the neural network, wherein:
the update to the neural network is intended to be used for updating the neural network; and
the updated neural network is intended to be active and used to enhance or filter decoded one or more media units that are within a temporal scope determined with the third enhancement information message, a spatial scope determined with the third enhancement information message, or a spatio-temporal scope determined with the third enhancement information message, wherein the third enhancement information message indicates that the updated neural network is active for use.

20. The apparatus of claim 19, wherein the container comprises a supplemental enhancement information (SEI) network abstraction layer (NAL) unit and the first and second enhancement information messages comprise SEI messages.

21. The apparatus of claim 20, wherein the instructions, when executed by the at least one processor, cause the apparatus at least to:
encode, within the container, an identifier for the neural network;
encode, within the media bitstream, a filter activation SEI message;
wherein the third enhancement information message encoded within the media bitstream comprises the filter activation SEI message;

encode, within the filter activation SEI message, the identifier for the neural network; and indicate, within the filter activation SEI message, activation of the neural network identified by the identifier within the temporal scope determined by the filter activation SEI message, the spatial scope determined by the filter activation SEI message, or the spatio-temporal scope determined by the filter activation SEI message.

22. The apparatus of claim 19, wherein the temporal scope, the spatial scope, or the spatio-temporal scope comprises:

first one or more frames of the decoded one or more media units, or one or more areas within second one or more frames of the decoded one or more media units.

\* \* \* \* \*